United States Patent [19]

Bierer

[11] Patent Number: 5,753,790
[45] Date of Patent: May 19, 1998

[54] HYPOGLYCEMIC AGENT FROM CRYPTOLEPIS

[75] Inventor: Donald E. Bierer, Daly City, Calif.

[73] Assignee: Shaman Pharmaceuticals, Inc., South San Francisco, Calif.

[21] Appl. No.: 472,020

[22] Filed: Jun. 6, 1995

Related U.S. Application Data

[62] Division of Ser. No. 314,188, Sep. 28, 1994.
[51] Int. Cl.[6] .............................. C07D 209/80; C09B 7/00
[52] U.S. Cl. ....................................................... 548/420
[58] Field of Search ............................................ 548/420

[56] References Cited

U.S. PATENT DOCUMENTS

| | | | |
|---|---|---|---|
| 3,374,264 | 3/1968 | Uskokovic et al. | 560/47 |
| 4,826,850 | 5/1989 | Yamato | 514/284 |

FOREIGN PATENT DOCUMENTS

| | | | |
|---|---|---|---|
| 0 376 166 A1 | 7/1990 | European Pat. Off. | C07D 221/18 |
| 5-306284 | 11/1993 | Japan | C07D 47/164 |
| WO 94/18203 | 8/1994 | WIPO | C07D 487/22 |

OTHER PUBLICATIONS

Baldwin and Magnus (eds.), 1994, in *Organic Syntheses Based on Name Reactions and Unnamed Reactions*, vol. 11, p. 36.
Blount et al., 1929, "Stereoisomerism in polycyclic systems. Part IV", J Chem Soc pp. 1975–1987.
Chang et al., 1992, "Synthesis of 7-substituted indolo[3, 2-β]-quinoline derivatives", Heterocycles 33(1):147–152.
Degutis and Ezyarskaite 1986. "Alkylation of quindoline and quindoline-11-carboxylic acid", Khimiya Geterotsiklicheskikh Soedinenii 10:1375–1379.
Desarbre and Merour, 1994, "Synthesis and reactivity of 1-substituted-3H-pyrrolo[2,3-β] pyridin-3-one", Tetrahedron Letters 35(13):1995–1998.
Ezyarskaite, 1989, "On the synthesis of 7-bromoquindoline derivatives", Izv Khim 22:101–105.
Galun et al., 1979, "Derivatives of indole-3-oxyacetic acid", J Heterocyclic Chem 16:641–643.
Giraud, 1879, "Sur quelques dérivés de l'indigotine", Comptes Rendus pp. 104–105.
Giraud, 1880, "Préparation de l'indoline et de ses composés", Comptes Rendus pp. 1429–1430.
Görlitzer and Weber, 1980, "11–oxo–5,11–dihydro–benzothieno[3,2–b][1] chinoline, S,S–dioxide und thionierungsprodukte", Arch Pharm 314:76–84.
Görlitzer and Weber, 1982, "Hemmung der thrombocytenaggregation durch anellierte chinoline mit 3–dimethylaminopropylmercapto–substituenten", Arch Phar 315:532–537.
Görlitzer and Weber, 1981, "1O–hydroxy–1OH–indolo[3, 2–b]chinollin–5–oxid ('Dioxychindolin')", Arch Pharm 314:850–852.
Görlitzer and Weber, 1980, "Anellierte chinoline III), 11–oxo–5,11–dihydro–benzothieno–[3,2–b][1] chinoline", Arch Pharm 313:27–34.
Görlitzer et al., 1994, "Anti–malaria active 1OH–indolo[3, 2–β]quinolin–11–ylamines. Part I. Phenol–Mannich–bases of the amodiaquine and cycloquine type", Pharmazie 49:231–235.
Görlitzer and Weber, 1981, "1OH–indolo[3,2–b]chinolin", Arch Pharm 314:852–861.

(List continued on next page.)

*Primary Examiner*—John Rollins
*Attorney, Agent, or Firm*—Pennie & Edmonds

[57] ABSTRACT

The use of extracts from Cryptolepis sp. or quinodoline alkaloids such quindoline and cryptolepine contained therein as hypoglycemic agents, as well as methods for obtaining the hypoglycemic agents are described. According to a preferred embodiment, the extracts are derived from *Cryptolepis sanguinolenta*. As hypoglycemic agents, the extracts or quindoline alkaloids such as quindoline or cryptolepine are useful for treating insulin-dependent (type I) and non-insulin-dependent (type II) diabetes.

1 Claim, 9 Drawing Sheets

OTHER PUBLICATIONS

Görlitzer et al., 1995, "Gegen malaria wirksame 1OH–indolo[3,2–b]chinolin–11–yl–amine", Pharmazie 50:105–111.

Görlizter, 1979, "Anellierte chinolone II, N– und O–alkylierungsprodukte", Arch Pharm 312:254–261.

Holt and Petrow, 1948, "Carbazoles, carbolines, and related compounds. Part III. Quinindoline derivatives", pp. 922–924.

Holt and Petrow, 1947, "Carbazoles, carbolines, and related compounds. Part I. Quindoline derivatives", pp. 607–611.

Holt and Petrow, 1948, "Carbazoles, carbolines, and related compounds. Part II. Transformations of some quarternary salts of quindoline", pp. 919–922.

Jezerskaite et al., 1989, "New heterocyclic sensitizers for electrophotography", Izv Khim 22:113–121.

Kempter et al., 1963, Z Chem 3:352–353.

Merour et al., 1982, "Syntheses of 2(5)–substituted 1–acetyl–3–oxo–2,3–dihydroindoles, 3–acetoxy–1–acetylindoles, and of 2–methyl–5–methoxyindole–3–acetic acid", Synthesis 12:1053–1056.

Mooradian et al., 1949, "A new series of testosterone esters", J Amer Chem Soc. 71:3372–3374.

Nenitzescu and Raileanu, 1958, "Synthesen des heteroauxins, des tryptamins und des serotonins", Chem Ber 91:1141–1145.

Ossman et al., 1988, "Synthesis of 2–cyanomethyl–3, 1–benzoxazin–4(H)–one", Egypt J Chem 31(3):381–385.

Schoen and Bogdanowicz–Szwed, 1964, "The reaction of α–indanone anils with phenylisocyanate. Anilides of 1–arylamino–indene–2–carboxylic acids", Roczniki Chemii Ann Soc Chim Polonorum 38:425–435.

Schulte et al., 1972, "Kondensierte indole aus 2–chlorindoaldehyd–(3)", Arch Pharmaz 305:523–533.

Schutzenberger, 1877, "Note sur un nouveau dérivé de l'indigotine", Comptes Rendus pp.147–149.

Sevodin et al., 1982, "New methods for the synthesis of quindolines on the basis of 1,5–diketones of the indolinone series", Chem Heterocyclic Compounds 18(8):865.

Sevodin et al., 1984, "New method of synthesis of quindolines from 1,5–diketones of the indoline series", Chem Heterocyclic Comp 20(12):1374–1380.

Sunder and Peet, 1978, "Synthesis of benzofuro[3,2–β] quinolin–6(11H)one and derivatives". J Heterocyclic Chem 15:1379–1382.

Takeuchi et al., 1991, "Synthesis and antitumor activity of 7–(N–glycosylamino)–indolo[3,2–β]quinolines", Chem Pharm Bull 39(6):1629–1631.

Takeuchi et al., 1992, "Synthesis and antitumor activity of fused quinoline derivatives. III. Novel N–glycosylamino–indolo[3,2–β]quinolines", Chem Pharm Bull 40(6):1481–1485.

Yamato et al., 1989, "Synthesis and antitumor activity of fused tetracyclic quinoline derivatives", J Med Chem 32:1295–1300.

Yamato et al., 1992, "Synthesis and antitumor activity of fused quinoline derivatives. II. Novel 4– and 7–hydroxyindolo[3,2–β]quinolines", Chem Pharm Bull 40(2):528–530.

Yamato et al., 1990, "Synthesis and antitumor activity of fused quinoline derivatives", Chem Pharm Bull 38(11):3048–3052.

Paulo et al., 1994, "In vitro antibacterial screening of Cryptolepis sanguinolenta alkaloids", J Ethnopharmacol 44:127–130.

Oyekan and Ablordeppey, 1993, "The mechanism(s) of the antiaggregatory effects of cryptolepine: The role of cyclic adenosine monophosphate and cellular $Ca^{2+}$", Gen Pharmacol 24(2):461–469.

Spitzer et al., "Total Assignment of the proton and carbon NMR spectra of the alkaloid quindoline—Utilization of HMQC–TOCSY to indirectly establish protonated carbon––protonated carbon connectivities", J Heterocyclic Chem 28:2065–2070.

Wilson et al., 1922, "Polynuclear Heterocyclic aromatic types. Part I. Some indenoquinoline derivatives", J Chem Soc pp. 827–839.

Fichter and Rohner, 1910, "Über einige derivate des chindolins", Chem. Ber. 43:3489–3499.

Fichter and Probst, 1907, "Zur kenntnis des methyl–chindolanols", Chem. Ber. 40:3478.

Okeyam, 1994, Role of the Endothelium and Cyclic GMP in Renal Vasodilator Responses to Cryptolepine in Rats, J. Cardiovasc. Pharmacol. 23:602–611.

Oyekan and Ablordeppey, 1993, Effects of Cryptolepine on Collagen–Induced Aggregation and on the Mobilization and Metabolism of Arachidonic Acid by Rabbit, Gen. Pharmac. 24:1285–1290.

Rauwald et al., 1992, Cryptolepis sanguinolenta:Antimuscarinic Properties of Cryptolepine and the Alkaloid Fraction at M1,M2 and M3 Receptors, Planta Medica, 58:486–488.

Cimanga et al., 1991, Biological Activities of Cryptolepine, An Alkaloid from Cryptolepis sanguinolenta, Planta Medica 57 Supp. 2 A98–A99.

Tackie et al., 1991, Assignment of the Proton and Carbon NMR Spectra of the Indoloquinoline Alkaloid Cryptolepine, J. Heterocycl. Chem. 28:1429–1435.

Ablordeppy et al., 1990, $^1$H–NMR and $^{13}$C–NMR Assignments of Cryptolepine A 3: 4–Benz–δ–carboline Derivative Isolated from Cryptolepis sanguinolenta,Planta Medica 56:416.

Oyekan and Okafor, 1989, Effects of Cryptolepine Alone and in Combination with Dipyridamole on a Mouse Model of Arterial Thrombosis, J. Ethnopharmacology 27:141–148.

Potential Antimalarial in Ghanian Plant, IMS Pharmaceutical Marketletter, May 7, 1984, p. 13.

Cryptolepine Hydrochloride, Drugs Future, 1982, 7(7):466.

Bamgbose and Noamesi, 1981, Studies on Cryptolepine, Planta Medica 41:392–396.

Noamesi et al., 1980, The Alpha–Adrenoceptor Blocking Properties of Cryptolepine on the Rat Isolated Vas Deferens, Planta Medica 39:51–56.

Gunatilaka et al., 1980, Studies on Medicinal Plants of Sri Lanka, Planta Medica, 39:66–72.

Boakye–Yiadom et al., 1979, Cryptolepine Hydrochloride Effect on Staphylococcus aureus, J. Pharm. Sci. 68:1510.–1514.

Dwuma–Badu et al., 1978, Constituents of West African Medicinal Plants XX: Quindoline from Cryptolepis sanguinolenta, J. Pharm. Sci. 67:433–434.

Gellert et al., 1951, Die Konstitution des Alkaloids Cryptolepin, Helv. Chim. Acta 34:642–651.

Raymond–Hamet et al., 1938, Pharmacologie—Sur les Effects Hypotenseurs et Vaso–dilatateurs de la Cryptolepine, C.R. Acad. Sci. 207:1015–1018.

Raymond–Hamet et al., 1937, Sur Quelques Proprietes Physiologiques des Alcaloides du *Crytloepis sanguinolenta* Schlechter, C.R. Soc. Biol. 126:768–770.

Clinquart et al., 1929, Sur la compesition chimique de *"Cryptolepis triangularis"* plante congolaise, Bull. Acad. R. Med. Belg. 12:627–635.

Fichter and Boehringer, 1906, Ueber Chindolin, Chemische Berichte 39:3932–3942.

HYPOGLYCEMIC AGENT FROM CRYPTOLEPIS

This is a division of application Ser. No. 08/314,188, filed Sep. 28, 1994.

FIELD OF THE INVENTION

This invention pertains to the use of a hypoglycemic agent from Cryptolepis sp., including, but not limited to *C. triangularis* and *C. sanguinolenta*, and quindoline alkaloids contained therein, such as quindoline and cryptolepine, for the treatment of diabetes mellitus.

BACKGROUND OF THE INVENTION

Compounds of the quindoline family of alkaloids, e.g. quindoline:

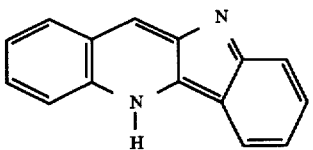

and cryptolepine:

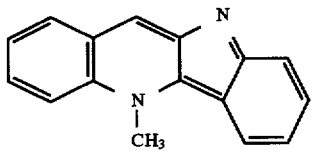

were first synthesized in 1906 (Fitchter, F. and Boehringer, R., Chemische Berichte 39, 3932 (1906)).

the natural product cryptolepine was first isolated from the plant *Cryptolepis triangularis* of the family Periplocacese in 1929 (Clinquart, E., Bull. Acad. R. Med. Belg. 12, 6237 (1929)). Cryptolepine was reisolated from *Cryptolepis sanguinolenta* in 1951 (Gellert, E., Rayond-Hamet, Schlittler, E., Helv. Chim. Acta 34, 642 (1951)) and again in 1978 together with quindoline and other uncharacterized alkaloids (Dwuma-Badu, D., Ayim, J. S. K., Fiagbe, N. I. Y., Knapp, J. E., Schiff Jr., P. L., and Slatkin, D. J., J. Pharm. Sci. 67, 433 (1978)). In a study of Sri-Lankan medicinal plants, cryptolepine was identified as the major alkaloid in *Sida acuta* (Gunatilaka, A. A., Planta Medica 39, 66 (1980)).

Proton and carbon n.m.r. (DMSOd$_6$) spectra for cryptolepine were assigned by Tackie, A. N., Sharaf, M. H. M., Schiff Jr., P. L., Boye, G. L., Couch, R. C., and Martin, G. E. (J. Heterocycl. Chem 28, 1429 (1991)); and by Ablordeppy, S. Y.; Hufford, C. D.; Borne, R. F., and Dwuma-Badu, D. Planta. Medica. 56, 416 (1990).

A study conducted in 1937 described marked hypothermia in dogs after administration of cryptolepine and noted and antagonistic effect to epinephrine characterized by decreased hypertension and renal vasoconstriction; a lethal dose was determined in guinea pigs after i.p. injection as 120 mg/kg (Raymond-Hamet, C., C. R. Soc. Biol. 126, 768 (1937)). A 1938 study showed a marked and protracted hypotensive response in vasectomized dogs after i.v. administration of cryptolepine (Raymond-Hamet, C., C. R. Acad. Sci., 208, 105 (1938)).

A report claimed that cryptolepine possesseed hypotensive and antibacterial properties (Drugs Future, 7(7), 466 (1982). More detailed antimicrobial activities for alcoholic extracts of *Cryptolepis sanguinolenta* were described (Boakye-Yiadom, K. and Heman-Ackah, S. M., J. Pharm. Sci. 68, 1510 (1979)).

In 1980, a paper described the noradrenoreceptor antagonism of cryptolepine in isolated rat vas deferens (Noamesi, B. K. and Bangbose, S. O. A., Planta Media 39, 51 (1980)). Cryptolepine's antiinflammatory action was reported in 1981 by the same researchers who identified prostaglandin E2 antagonism as the cause. (Bamgbose, S. O. A. and Noamesi, B. K., *Planta Medica*, 41, 392 (1981)).

According to the West African Pharmaceutical Federation *Cryptolepis sanguinolenta* has been widely used in folk medicine for the treatment of maleria, gonorrhoea, and hypertension. The antimalarial activity of Cryptolepis roots is linked to the presence of cryptolepine. As an antiinflammatory agent it is claimed to be as active as piroxicam or indomethacin (IMS Pharmaceutical Marketletter, May 7, 1984, p. 13.)

The effects of cryptolepine alone and in combination with dipyridamole were studied in a mouse model of arterial thrombosis in 1989 (Oyekam, A. O. and Okafor, J. P. O., J. Ethnopharmacology 27, 141 (1989)).

Cryptolepine was found to possess high anti-Candida activity as well as pronounced activity against Gram-positive bacteria. Additionally, weak activity against some Gram-negative bacteria but no antiviral activity was observed (Cimanga, K., Piaters, L., Clayes, M., Vanden Berghe, D., and Vlientick, A. J., Planta Media 57, Supp. 2, A98, (1991)).

More recently, cryptolepine and related alkaloids were found to possess antimuscarinic activity at the M1, M2, and M3 receptors (Rauwalk, H. W., Kober, N. C., Mutschler, E., and Lambrecht, G., Planta Medica, 58, 486 (1992)).

Cryptolepine has been described to have an effect on collagen-induced platelet aggregation and on the mobilization and metabolism of archidonic acid in a rabbit model (Oyekan, A. O. and Ablordeppey, S. Y., Gen. Pharmacol. 24, 1285 (1993)). Cryptolepine's hypotensive and vasodilator mechanisms of action on perfused rat kidney were further described (Oyekan, A. O., J. Cardiovasc. Pharmacol., 23, 602 (1994)).

Citation or identification of any reference in Section 2 of this application shall not be construed as an admission of prior art to the present invention.

To the knowledge of the inventors, no prior study has described any hypoglycemic activity of extracts of Cryptolepis sp. nor was there any suggestion in the prior art that quindoline alkaloids such as cryptolepine or quindoline would be useful as hypoglycemic agents.

SUMMARY OF THE INVENTION

The present invention provides a method for the use of extracts from Cryptolepis sp. and compounds of the quindoline family of alkaloids such as quindoline, cryptolepine, etc., as well as pharmaceutically acceptable salts thereof, as hypoglycemic agents or as agents to lower triglyceride levels, particularly in diabetic subjects.

Thus, the invention encompasses a method for using a compound having the formula:

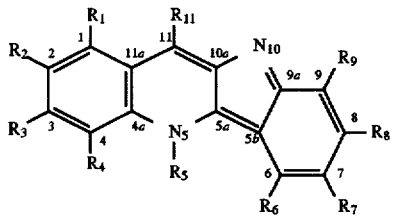

said compound selected from group consisting of:

(a) where $R_1-R_{11}=H$;

(b) where $R_1-R_4$ and $R_6-R_{11}=H$, and $R_5=CH_3$;

(c) where $R_1-R_4$ and $R_6-R_{11}=H$, and $R_5$ is selected from the group of ethyl, isopropyl, benzyl, 4-hydroxybenzyl, 4-dimethylaminobenzyl, 4-chlorobenzyl, phenyl, 2-chlorophenyl, 3-chlorophenyl, 2-bromophenyl, 3-bromophenyl, 2-fluorophenyl, 3-fluorophenyl, 2-iodophenyl, 3-iodophenyl, 4-iodophenyl, 2-hydroxyphenyl, 3-hydroxyphenyl, 2-dimethylaminophenyl, 3-dimethylaminophenyl, 2-methoxyphenyl, 3-methoxyphenyl, and 4-methoxyphenyl, 4-hydroxyphenyl, 4-dimethylaminophenyl, 4-chlorophenyl, 2-pyridino, 3-pyridino, 4-pyridino, 2-imidazol, 4-imidazol, 2-hydroxybenzyl, 3-hydroxybenzyl, 2-dimethylaminobenzyl, 3-dimethylaminobenzyl, 2-methoxybenzyl, 3-methoxybenzyl, 4-methoxybenzyl, 2-chlorobenzyl, 3-chlorobenzyl, 2-bromobenzyl, 3-bromobenzyl, 4-bromobenzyl, 2-fluorobenzyl, 3-fluorobenzyl, 4-fluorobenzyl, 2-iodobenzyl, 3-iodobenzyl, 4-iodobenzyl, 2-pyridylmethyl, 3-pyridylmethyl, 4-pyridylmethyl, 2-imidazolylmethyl, 4-imidazolylmethyl, 4-bromophenyl, 4-fluorophenyl, cyclopropyl, and isobutyl;

(d) where $R_1$, $R_4$ and $R_6-R_{11}=H$, $R_2=R_3=-CH_2-O-CH_2-$, and $R_5$ is selected from the group consisting of ethyl, isopropyl, benzyl, 4-hydroxybenzyl, 4-dimethylaminobenzyl, 4-chlorobenzyl, phenyl, 2-chlorophenyl, 3-chlorophenyl, 2-bromophenyl, 3-bromophenyl, 2-fluorophenyl, 3-fluorophenyl, 2-iodophenyl, 3-iodophenyl, 4-iodophenyl, 2-hydroxyphenyl, 3-hydroxyphenyl, 2-dimethylaminophenyl, 3-dimethylaminophenyl, 2-methoxyphenyl, 3-methoxyphenyl, 4-methoxyphenyl, 4-hydroxyphenyl, 4-dimethylaminophenyl, 4-chlorophenyl, 2-pyridino, 3-pyridino, 4-pyridino, 2-imidazol, 4-imidazol, 2-hydroxybenzyl, 3-hydroxybenzyl, 2-dimethylaminobenzyl, 3-dimethylaminobenzyl, 2-methoxybenzyl, 3-methoxybenzyl, 4-methoxybenzyl, 2-chlorobenzyl, 3-chlorobenzyl, 2-bromobenzyl, 3-bromobenzyl, 4-bromobenzyl, 2-fluorobenzyl, 3-fluorobenzyl, 4-fluorobenzyl, 2-iodobenzyl, 3-iodobenzyl, 4-iodobenzyl, 2-pyridylmethyl, 3-pyridylmethyl, 4-pyridylmethyl, 2-imidazolylmethyl, 4-imidazolylmethyl, 4-bromophenyl, 4-fluorophenyl, cyclopropyl and isobutyl;

(e) where $R_1=R_4$, and $R_6-R_7$ and $R_{10}-R_{11}=H$, $R_4=R_4=-CH_2-O-CH_3-$, and $R_5$ is selected from the group consisting of ethyl, isopropyl, benzyl, 4-hydroxybenzyl, 4-dimethylaminobenzyl, 4-chlorobenzyl, phenyl, 2-chlorophenyl, 3-chlorophenyl, 2-bromophenyl, 3-bromophenyl, 2-fluorophenyl, 3-fluorophenyl, 2-iodophenyl, 3-iodophenyl, 4-iodophenyl, 2-hydroxyphenyl, 3-hydroxyphenyl, 2-dimethylaminophenyl, 3-dimethylaminophenyl, 2-methoxyphenyl, 3-methoxyphenyl, 4-methoxyphenyl, 4-hydroxyphenyl, 4-dimethylaminophenyl, 4-chlorophenyl, 2-pyridino, 3-pyridino, 4-pyridino, 2-imidazol, 4-imidazol, 2-hydroxybenzyl, 3-hydroxybenzyl, 2-dimethylaminobenzyl, 3-dimethylaminobenzyl, 2-methoxybenzyl, 3-methoxybenzyl, 4-methoxybenzyl, 2-chlorobenzyl, 3-chlorobenzyl, 2-bromobenzyl, 3-bromobenzyl, 4-bromobenzyl, 2-fluorobenzyl, 3-fluorobenzyl, 4-fluorobenzyl, 2-iodobenzyl, 3-iodobenzyl, 4-iodobenzyl, 2-pyridylmethyl, 3-pyridylmethyl, 4-pyridylmethyl, 2-imidazolylmethyl, 4-imidazolylmethyl, 4-imidazolymethyl, 4-bromophenyl, 4-fluorophenyl, cyclopropyl and isobutyl;

(f) where $R_1-R_3$ and $R_6-R_{11}=H$, and $R_4-R_5=-CH_2CH_2-$;

(g) where $R_1-R_3$ and $R_6-R_{11}=H$, and $R_4-R_5=-CH_2CH_2CH_2-$;

(h) where $R_1-R_4$ and $R_6-R_{11}=H$, $R_5=CH_3$, and 10a, 11=dihydro;

(i) where $R_1-R_4$ and $R_6-R_{11}=H$, $R_5=CH_3$, and 5a, 5b=dihydro;

(j) where $R_1-R_4$ and $R_6-R_{11}=H$, $R_5=CH_3$, and 5a, 5b, 10a, 11=tetrahydro.

(k) where $R_1-R_{11}=H$, and 9a,10=dihydro; and (l) where $R_1-R_{11}=H$, and 10-methyl as a hypolycemic agent.

By "10a,11=dihydro" is meant those compounds which bear hydrogen atoms at carbons 10 and 11. By "5a,5b=dihydro" is meant those compounds which bear hydrogen atoms at carbons 5a and 5b. By "5a,5b,10a,11=tetrahydro" is meant those compounds which bear hydrogen atoms at carbons 5a,5b,10a and 11. by "10-methyl" is meant those compounds which bear a methyl group on $N_{10}$. In the latter case, the hydrogen atom at $R_5$ may be optionally absent.

The invention also encompassses a method for using a compound of formula I as a triglyceride lowering agent in diabetic subjects. The invention also encompasses novel compounds of formula I as well as pharmaceutical compositions comprising such compounds as well as methods for using such compounds and pharmaceutically acceptable salts thereof.

The invention further encompasses pharmaceutical compositions and methods for using the extracts, or quindoline alkaloids such as quindoline or cryptolepine or pharmaceutically acceptable salts, for the treatment of insulin-dependent diabetes mellitus and non-insulin dependent diabetes mellitus in mammals, including humans. Also encompassed are methods for using the hypoglycemic agents to reduce blood glucose in mammals, including humans, in situations of acute stress.

According to the first embodiment of the invention, a therapeutically effective hypoglycemic agent is prepared by a method comprising:

(a) washing a root of Cryptolepis sp. with an alcoholic solvent to obtain an alkaloid salt-containing alcoholic solution; and (b) concentrating the alkaloid salt-containing alcoholic solution to obtain an alkaloid salt-containing residue which is useful as a hypoglycemic agent. According to one mode of the embodiment, the hypoglycemic agent is prepared by said method, further comprising:

(c) diluting the alkaloid salt-containing residue with water to obtain an alkaloid salt-containing aqueous solution;

(d) washing the alkaloid salt-containing aqueous solution with a non-polar organic solvent to remove neutral extractables therefrom;

(e) washing the alkaloid salt-containing aqueous solution of step (d) with base to obtain a free base-containing aqueous solution;

(f) extracting the free base-containing aqueous solution with a non-polar organic solvent to obtain a free base-containing organic solution;

(g) concentrating the free base-containing organic solution to obtain a free base-containing residue; and (h) purifying the free base-containing residue to obtain a hypoglycemic agent.

According to a second embodiment of the invention, a therapeutically effective hypoglycemic agent is prepared by a method comprising:

(a) washing a root of Cryptolepis sp. with an organic solvent to obtain an alkaloid salt-containing marc, said alkaloid salt-containing marc being free of neutral extractables;

(b) wetting the alkaloid salt-containing marc with base to obtain a free base-containing marc;

(c) washing the free base-containing marc with an alcoholic solvent to obtain a free base-containing alcoholic solution;

(d) concentrating the free base-containing alcoholic solution to obtain a free base-containing residue; and (e) purifying the free base-containing residue to obtain a hypoglycemic agent.

Other embodiments of the present invention include washing a root of Cryptolepis sp. with a polar alcoholic solvent, an acidic solution or water to obtain an extract, concentrating the extract and optionally purifying the concentrated extract to obtain a hypoglycemic agent of the present invention.

The present invention may be understood more fully by reference to the following figures, detailed description and illustrative examples which are intended to exemplify non-limiting embodiments of the invention.

DETAILED DESCRIPTION OF THE INVENTION

5.1 PROCESS FOR PREPARING HYPOGLYCEMICALLY ACTIVE EXTRACTS

Figure 1:
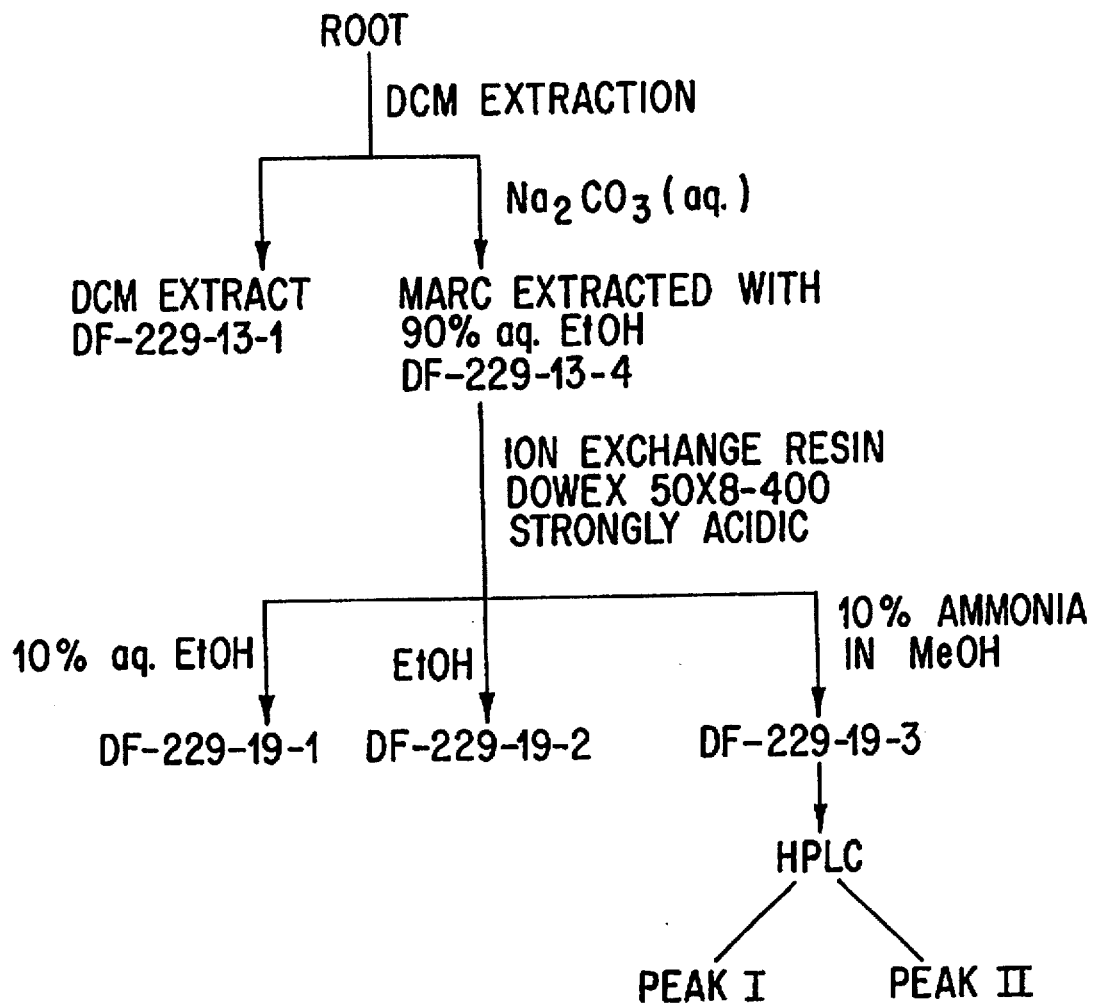
FIG. 1 is a flow-chart describing a method for isolation of a hypoglycemically active fraction from Cryptolepis sp.

According to the present invention, a hypoglycemic extract can be prepared by Cryptolepis sp., including, but not limited to *C. triangularis* and *C. sanguinolenta*.

According to a first embodiment, a sample of Cryptolepis sp. root is washed with a polar alcoholic solvent to extract alkaloid salts therefrom. Suitable alcoholic solvents include, but are not limited to methanol, ethanol, 2-methoxyethanol, 1-propanol, 2-propanol, iso-butanoyl, sec-butanol and the like. The alcoholic solvents may optionally be diluted with water in order to adjust the polarity and hence the alkaloid salt solubility thereof. The aqueous content of the alcoholic solvents may range from 0–25%, preferably 0–10%. Most preferably, the alcoholic solvent is 90% aqueous ethanol.

The alkaloid salt-containing alcoholic solution is then concentrated so as to remove the alcoholic solvent therefrom. Concentration may optionally occur at elevated temperature, in vacuo, or both, so as to expedite the removal of solvent.

The resulting alkaloid salt-containing residue is diluted with water and the resulting alkaloid salt-containing aqueous solution is washed with a non-polar organic solvent to remove neutral extractables therefrom. By "neutral extractables" is meant any non-salts which are soluble in non-polar organic solvents. Suitable non-polar organic solvents which may be used include, but are not limited to diethyl ether, ethyl acetate, isoamyl acetate, benzene, toluene, 2-butanone, 4-methyl-2-pentanone, chlorinated hydrocarbons such as dichloromethane, chloroform, carbon tetrachloride, 1,2-dichloroethane, tetrachloroethylene, and other non-polar organic solvents known to those of ordinary skill in the art.

The resulting alkaloid salt-containing aqueous solution is then washed with base to free the alkaloid from its corresponding salt. Such suitable bases include, but are not limited to alkali metal carbonates, such as lithium, sodium, or potassium carbonate, alkali metal bicarbonates, such as lithium, sodium, or potassium bicarbonate, alkali metal hydroxides, such as lithium, sodium, or potassium hydroxide, or mixtures thereof. Preferably, the bases contemplated by the present invention are used as aqueous solutions which may range in concentration from 0.001 to 12M.

The resulting free base-containing aqueous solution is then extracted with a non-polar organic solvent to give a free base-containing organic solution. The non-polar organic solvent can be chosen from the group of such solvents described above.

The free base-containing organic solution is then concentrated to give a residue comprising alkaloids which are freed from their corresponding salt. Concentration may proceed at room temperature or at an elevated temperature which may accelerate the removal of solvent. In addition, concentration may occur at ambient pressure, or preferably in vacuo.

The free base-containing residue is then purified to provide the hypoglycemically active composition of the present invention. Suitable methods of purification include, but are not limited to recrystallization from solvents and solvent mixtures known to those of skill in the art, ion exchange such as through a column containing DOWEX resin, elution chromatography and combinations thereof. Methods of elution chromatography include, but are not limited to preparative thin-layer chromatography, conventional silica gel chromatography, and high performance liquid chromatography. Purification of the free base-containing residue by any of the above mentioned means may optionally separate the residue into various fractions, each of which may function alone or in combination with any other fraction or fractions as the hypoglycemic agent of the present invention. The hypoglycemic agent of the present invention contains quindoline, cryptolepine or mixtures thereof.

In the event that the hypoglycemic agent obtained from the above purification method contains a mixture of quindoline and cryptolepine, it may be desired to separate the alkaloids into their separate components. In such a case, the hypoglycemic agent may optionally be further purified, by such means as are stated above, to obtain quindoline or cryptolepine in substantially pure form. Preferably, the latter purification step involves high performance liquid chromatography using a water/acetonitrile/isopropanol gradient. According to a preferred embodiment, reverse phase high performance liquid chromatography is performed using C-18 derivatized polymethacrylate (highly cross-linked). According to another embodiment, cross-linked polystyrene is used.

According to a second embodiment of the invention, the hypoglycemic agent is prepared as follows:

Roots of Cryptolepis sp. are first washed with a non-polar organic solvent to remove neutral extractables therefrom. By "neutral extractables" is meant any non-salts which are soluble in non-polar organic solvents. Suitable non-polar organic solvents which may be used include, but are not limited to diethyl ether, ethyl acetate, isoamyl acetate, benzene, toluene, 2-butanone, 4-methyl-2-pentanone, chlorinated hydrocarbons such as dichloromethane, chloroform, carbon tetrachloride, 1,2-dichloroethane, tetrachloroethylene, and other non-polar organic solvents known to those of ordinary skill in the art. Preferably, dichloromethane is used. The root is washed with the non-polar organic solvent primarily to remove any neutral contaminants which may adversely affect the purity and efficacy of the hypoglycemic agent the present invention. Prior to washing, the roots may optionally be ground, for example in a Wiley mill, or otherwise reduced in overall size, so as to increase the effective surface area of the root available to the solvent.

After washing with the non-polar organic solvent, the resulting alkaloid salt-containing marc is wetted with a base, so as to free alkaloids contained therein from corresponding acid salts. Suitable bases which may be used in this capacity include, but are not limited to alkali metal carbonates, such as lithium, sodium, or potassium carbonate, alkali metal bicarbonates, such as lithium, sodium, or potassium bicarbonate, alkali metal hydroxides, such as lithium, sodium, or potassium hydroxide, or mixtures thereof. Preferably, the bases contemplated by the present invention are used as aqueous solutions which may range in concentration from 0.0001 to 12M. Prior to wetting, the marc may optionally be dried. After wetting with the base, the alkaloids which have been freed from their corresponding acid salts are extracted from the free base-containing marc with a polar alcoholic solvent as described above. The alcoholic solvents may optionally be diluted with water to adjust the polarity thereof. The aqueous content of the alcoholic solvents may range from 0–25%, preferably 0–10%. Preferably, the solvent used to extract from the roots the alkaloids which were freed from their corresponding salts is a mixture of ethanol and water. Most preferably, the solvent system is 90% aqueous ethanol. Prior to extracting, the root may optionally be re-dried, preferably by lyophilizing.

The alcholic solution containing the alkaloids free from their corresponding salts is then concentrated to give a residue comprising such alkaloids. Concentration may proceed at room temperature or at an elevated temperature which may accelerate the removal of solvent. In addition, concentration may occur at ambient pressure, or preferably in vacuo.

The free base-containing residue is then purified to provide the hypoglycemic agent of the present invention. Suitable methods of purification include, but are not limited to recrystallization from solvents and solvent mixtures known to those of skill in the art, ion exchange such as through a column containing DOWEX resin, elution chromatography and combinations thereof. Methods of elution chromatography include, but are not limited to preparative thin-layer chromatography, conventional silica gel chromatography, and high performance liquid chromatography. Purification of the residue by any of the above-mentioned means may optionally separate the residue into various fractions, each of which can be screened for hypoglycemic activity. The hypoglycemic agent of the present invention contains quindoline, cryptolepine or mixtures thereof.

In the event that the hypoglycemic agent obtained from the above mentioned purification method contains a mixture of quindoline and cryptolepine, it may be desired to separate the mixture into its separate compounds. In such a case, the hypoglycemic agent may optionally be further purified, by such means as are stated above, to obtain quindoline or cryptolepine in substantially pure form. Preferably, the latter purification step involves high performance liquid chromatography using a water/acetonitrile/isopropanol gradient. (For an example of this embodiment, see FIG. 1).

According to a third embodiment of the invention, the hypoglycemic agent is prepared by washing Cryptolepis sp. roots with a polar alcoholic solvent. For example 10–25 g of crushed Cryptolepis sp. roots are agitated in approximately 1L of 90% aqueous ethanol for 24–72 hrs. The resulting extract is concentrated to obtain the hypoglycemic agent of the present invention. Suitable polar alcoholic solvents which may be used are those recited above. The alcoholic solvents may optionally be diluted with water to adjust the polarity thereof. The aqueous content of the alcoholic solvents may range from 0–25%, preferably 0–10%. Most preferably, the alcoholic solvent is 90% aqueous ethanol.

The resulting solution is then concentrated, by methods recited above, to obtain a residue. The residue is optionally purified, by methods recited above, to obtain the hypoglycemic agent of the present invention.

In the event that further purification of the hypoglycemic agent obtained from the above method is desired, the hypoglycemic agent may optionally be further purified, by such means as are stated above. Preferably, the latter purification step involves high performance liquid chromatography using a water/acetonitrile/isopropanol gradient.

According to a fourth embodiment of the invention, the hypoglycemic agent is prepared by washing Cryptolepis sp. roots with an aqueous acidic solution. For example, 10–100 g of crushed Cryptolepis sp. roots are agitated in approximately 1L of 1–10% acetic acid/water for 24–72 hrs. The resulting extracted is neutralized with a base mentioned above and concentrated to obtain the hypoglycemic agent of the present invention. The concentration of such a solution may range from 0.001 to 12M, preferably from 0.001 to 2M and most preferably from 0.01 to 1M. Suitable acids which may comprise the acidic aqueous solution include, but are not limited to carboxylic acids such as formic acid, acetic acid, citric acid, tartaric acid, oxalic acid, malic acid, succinic, ascorbic, gluconic and benzoic, inorganic acids such as hydrochloric acid, sulfuric acid, hydorbromic acid, hydroiodic acid, and orthophosphoric acid, phosphoric and other acids capable of forming stable alkaloid salts commonly known to those skilled in the art. Preferably, aqueous acetic acid is used.

The resulting alkaloid salt-containing aqueous solution is then concentrated, by methods recited above, to obtain an alkaloid salt-containing residue. Prior to concentration, the alkaloid salt-containing aqueous solution is washed with base, as recited above, to free the alkaloid from its corresponding salt and extracted with a non-polar organic solvent, as recited above, to give a free base-containing organic solution. After concentration, the residue is optionally purified, by methods recited above, to obtain the hypoglycemic agent of the present invention.

The hypoglycemic agent may optionally be further purified, by such means as are recited above. Preferably, the latter purification step involves high performance liquid chromatography using a water/acetonitrile/isopropanol gradient.

According to a fifth embodiment of the invention, the hypoglycemic agent is prepared by extracting Cryptolepis sp. roots with water. For example, 1.0–2.0 g of crushed Cryptolepis sp. roots are steeped in approximately 250 mL of water heated at 55°–65° C. for 5 minutes—24 hrs. The resulting extract comprises the hypoglycemic agent of the present invention. Suitable extraction temperatures range from 25°–100° C., preferably 45°–65° C., and most preferably 55°–65° C.

The resulting aqueous extract may optionally be concentrated, to obtain a concentrate having hypoglycemic activity. The concentrate can be further dehydrated for example, lyophililzed or spray dried to form a composition which upon rehydration with water, aqueous or other pharmaceutically acceptable excipient, can be used as a hypoglycemic agent. The concentrate is optionally purified, by methods described above, to obtain a hypoglycemic agent for use in the methods of the present invention. Prior to concentration, the extract can optionally be washed with base and/or extracted with a non-polar organic solvent as recited above.

It may be desired to separate the mixture into its separate components. In such a case, the hypoglycemic agent may optionally be further purified, by such means as are stated above, to obtain quindoline or cryptolepine in substantially pure form. Preferably, the latter purification step involves high performance liquid chromatography using a water/acetonitrile/isopropanol gradient.

5.2 ISOLATION OF QUINDOLINE, CRYPTOLEPINE OR MIXTURES THEREOF

The extracts of the present invention may be further purified so as to isolate a more pure extract or quindoline, cryptolepine or mixtures thereof from the extract. Preferably, the extract is purified by ion exchange with a highly acidic resin such as DOWEX followed by high-performance liquid chromatography over a neutral polystyrene matrix, thereby isolating from the extract quindoline, cryptolepine or mixtures thereof. Most preferably, the high-performance liquid chromatography column is eluted with water/acetonitrile/isopropanol. According to a preferred embodiment, reversed phase high performance liquid chromatography is performed using C-18 derivatized polymethacrylate (highly cross-linked). According to another embodiment, cross-linked polystyrene is used. As contemplated by the present invention, quindoline, cryptolepine or mixtures thereof may be used directly as hypoglycemic agents.

In a preferred mode of extraction, the roots of *Cryptolepis sanguinolenta* are extracted with a solution of 1% acetic acid in water so described by Ablordeppey et al. (Planta Medica, 56, 416 (1990)).

Alternatively, quindoline or cryptolepine can be obtained by methods of classical organic synthesis known by those of skill in the art (see Fichte, F. and Boehringer, R., Chem. Ber., 39, 3932 (1906)) for use according to the methods of the invention.

5.3 OTHER QUINDOLINE ALKALOIDS

According to the present invention, quindoline alkaloids having the generic structure below are also useful as hypoglycemic agents:

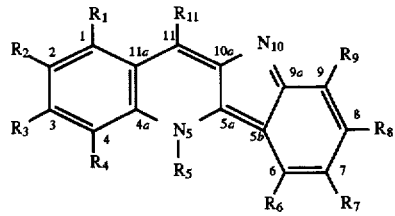

(a) where $R_1$–$R_4$ and $R_6$–$R_{11}$=H, and $R_5$ is selected from the group of ethyl, isopropyl, benzyl, 4-hydroxybenzyl, 4-dimethylaminobenzyl, 4-chlorobenzyl, phenyl, 2-chlorophenyl, 3-chlorophenyl, 2-bromophenyl, 3-bromophenyl, 2-fluorophenyl, 3-fluorophenyl, 2-iodophenyl, 3-iodophenyl, 4-iodophenyl, 2-hydroxyphenyl, 3-hydroxyphenyl, 2-dimethylaminophenyl, 3-dimethylaminophenyl, 2-methoxyphenyl, 3-methoxyphenyl, 4-methoxyphenyl, 4-hydroxyphenyl, 4-dimethylaminophenyl, 4-chlorophenyl, 2-pyridino, 3-pyridino, 4-pyridino, 2-imidazol, 4-imidazol, 2-hydroxybenzyl, 3-hydroxybenzyl, 2-dimethylaminobenzyl, 3-dimethylaminobenzyl, 2-methoxybenzyl, 3-methoxybenzyl, 4-methoxybenzyl, 2-chlorobenzyl, 3-chlorobenzyl, 2-bromobenzyl, 3-bromobenzyl, 4-bromobenzyl, 2-fluorobenzyl, 3-fluorobenzyl, 4-fluorobenzyl, 2-iodobenzyl, 3-iodobenzyl, 4-iodobenzyl, 2-pyridylmethyl, 3-pyridylmethyl, 4-pyridylmethyl, 2-imidazolylmethyl, 4-imidazolylmethyl, 4-bromophenyl, 4-fluorophenyl, cyclopropyl, and isobutyl;

(b) where $R_1$, $R_4$ and $R_6$–$R_{11}$=H, $R_2$=$R_5$=—$CH_3$— O—$CH_2$—, and $R_5$ is selected from the group consisting of ethyl, isopropyl, benzyl, 4-hydroxybenzyl, 4-dimethylaminobenzyl, 4-chlorobenzyl, phenyl, 2-chlorophenyl, 3-chlorophenyl, 2-bromophenyl, 3-bromophenyl, 2-fluorophenyl, 3-fluorophenyl, 2-iodophenyl, 3-iodophenyl, 4-iodophenyl, 2-hydroxyphenyl, 3-hydroxyphenyl, 2-dimethylaminophenyl, 3-dimethylaminophenyl, 2-methoxyphenyl, 3-methoxyphenyl, 4-methoxyphenyl, 4-hydroxyphenyl, 4-dimethylaminophenyl, 4-chlorophenyl, 2-pyridino, 3-pyridino, 4-pyridino, 2-imidazol, 4-imidazol, 2-hydroxybenzyl, 3-hydroxybenzyl, 2-dimethylaminobenzyl, 3-dimethylaminobenzyl, 2-methoxybenzyl, 3-methoxybenzyl, 4-methoxybenzyl, 2-chlorobenzyl, 3-chlorobenzyl, 2-bromobenzyl, 3-bromobenzyl, 4-bromobenzyl, 2-fluorobenzyl, 3-fluorobenzyl, 4-fluorobenzyl, 2-iodobenzyl, 3-iodobenzyl, 4-iodobenzyl, 2-pyridylmethyl, 3-pyridylmethyl, 4-pyridylmethyl, 2-imidazolylmethyl, 4-imidazolylmethyl, 4-bromophenyl, 4-fluorophenyl, cyclopropyl, and isobutyl;

(c) where $R_1$–$R_4$, $R_6$–$R_7$ and $R_{10}$–$R_{11}$=H, $R_8$=$R_9$=— $CH_2$—O—$CH_2$—, and $R_3$ is selected from the group consisting of ethyl, isopropyl, benzyl, 4-hydroxybenzyl, 4-dimethylaminobenzyl, 4-chlorobenzyl, phenyl, 2-chlorophenyl, 3-chlorophenyl, 2-bromophenyl, 3-bromophenyl, 2-fluorophenyl, 3-fluorophenyl, 2-iodophenyl, 3-iodophenyl, 4-iodophenyl, 2-hydroxyphenyl, 3-hydroxyphenyl, 2-dimethylaminophenyl, 3-dimethylaminophenyl, 2-methoxyphenyl, 3-methoxyphenyl, 4-methoxyphenyl, 4-hydroxyphenyl, 4-dimethylaminophenyl, 4-chlorophenyl, 2-pyridino, 3-pyridino, 4-pyridono, 2-imidazol, 4-imidazol, 2-hydroxybenzyl, 3-hydroxybenzyl, 2-dimethylaminobenzyl, 3-dimethylaminobenzyl, 2-methoxybenzyl, 3-methoxybenzyl, 4-methoxybenzyl, 2-chlorobenzyl, 3-chlorobenzyl, 2-bromobenzyl, 3-bromobenzyl, 4-bromobenzyl, 2-fluorobenzyl, 3-fluorobenzyl, 4-fluorobenzyl, 2-iodobenzyl, 3-iodobenzyl, 4-iodobenzyl, 2-pyridylmethyl, 3-pyridylmethyl, 4-pyridylmethyl, 2-imidazolylmethyl, 4-imidazolymethyl, 4-bromophenyl, 4-fluorophenyl, cyclopropyl, and isobutyl;

(d) where $R_1$-$R_3$ and $R_6$-$R_{11}$=H, and $R_6$-$R_5$=—$CH_2CH_2$—;

(e) where $R_1$-$R_3$ and $R_6$-$R_{11}$=H, and $R_4$-$R_5$=—$CH_2CH_2CH_2$—;

(f) where $R_1$-$R_4$ and $R_6$-$R_{11}$=H, $R_5$=$CH_3$, and 10a, 11=dihydro;

(g) where $R_1$-$R_4$ and $R_6$-$R_{11}$=H, $R_5$=$CH_3$, and 5a, 5b=dihydro;

(h) where $R_1$-$R_4$ and $R_6$-$R_{11}$=H, $R_5$=$CH_3$, and 5a, 5b, 10a, 11=tetrahydro, (i) where $R_1$-$R_{11}$=H, and 9a,10=dihydro; and (j) where $R_1$-$R_{11}$=H, and 10-methyl.

Compounds of the above structure can be prepared by several routes. For example, a suitably substituted anthranilic acid derivative may be condensed with an analogously substituted 3-hydroxyindole in the presence of Ba(OH)$_2$, followed by decarboxylation in the presence of potassium hydroxide and zinc to give substituted quindoline alkaloids (see, E. Giraud, *Compt. Rend.*, 85, 104 (1879) and F. Fichter and B. Rohner, *Chem. Ber.* 43, 3489 (1910)).

Alternatively, a substituted 1,2-(o-nitrophenyl)-1-cyanoethane may be heated in the presence of (NH$_4$)$_2$S in alcohol to further obtain substituted quindoline alkaloids (see, P. Gabriel and H. Eschenback, *Chem. Ber.*, 30 3020 (1897)).

Substituted quindoline alkaloids may also be obtained from substituted bis(o-nitrobenzyl) malonates which, after decarboxylation with alkali, may be heated in the presence of HI/P (F. Fichter and R. Boehringer, *Chem. Ber.*, 39, 3932 (1906)).

Dihydroquindolines may be obtained by reducing appropriately substituted quindoline alkaloids with tin in HCl (see, F. Fichter and R. Boeringer, *Chem. Ber.*, 39, 3932 (1906)).

Additionally, other routes to substituted quindolines may be applied (see, J. W. Armit and R. J. Robinson, *J. Chem. Soc.*, 121, 827 (1922); S. J. Holt and V. Petrow, *J. Chem. Soc.*, 607 (1947); E. Gellert, Raymond-Hamet and E. Schlittler, *Helv. Chim. Acta*, 34, 642 (1951); K. E. Schults, J. Reisch and U. Stoess, *Arch. Pharmar*, 305, 523 (1972); V. P. Sevodin, V. S. Velezhera, Y. V. Erofeav, N. N. Suvorov *Khim. Geterotsikl, Soedin.*, 1667 (1984); A. Buzas, J. Y. Merour, *Synthesis*, 458 (1989); Y. A. Degutis, A. B. Ezyarskaite, *Khim. Geterotsikl, Soedin.*, 1375 (1986); Y. Takeuchi, M. R. Chang, K. Masigaki, T. Tashiro, T. Tsuro, S. Tsukagoshi, M. Yamato. *Chem. Phar. Bull*, 40, 1481 (1992); M. R. Chang, Y. Takeuchi, K. Hashigaki, M. Yamato, *Heterocyctes* 33, 147 (1992); and M. Yamato, Y. Takeuchi, M. R. Chang, K. Hashiyaki, *Chem. Pharm. Bull.*, 40, 528 (1992).

The invention also encompasses novel compounds of formula I and pharmaceutically acceptable salts thereof, as well as compositions comprising such compounds and methods for their use.

5.4 METHODS FOR USE OF EXTRACTS OF CRYPTOLEPIS SP. AND QUINDOLINE ALKALOIDS SUCH AS CRYPTOLEPINE AND QUINDOLINE

Due to the potent activity of the extracts of Cryptolepis sp., obtained, as described in section 5.2 above, using an organic solution, a polar alcoholic solution, an aqueous acidic solution or an aqueous solution, as hypoglycemic agents (see Section 7, infra), the extracts are advantageously useful in veterinary and human medicine for therapeutic treatment of diabetes mellitus. Additionally, the extracts can be advantageously be used as hypoglycemic agents to reduce the blood glucose level in situations of acute stress such as experienced by animals or patients with hyperthermia, trauma, sepsis, and burns and undergoing general anesthesia. Hyperglycemia sometimes associated with severe head injury, cerebral thrombosis, encephalitis and heat stroke can also be therapeutically treated with these biologically active extracts. Additionally, the extracts are useful as hypoglycemic agents for rare cogenital metabolic glycogen storage disease associated with hyperglycemia.

Although the present inventors do not wish to be limited to any particular mechanism of action to explain the hypoglycemic activity of the hypoglycemic agents of the present invention, it is envisaged that the extracts or the quindoline or cryptolepine may advantageously be useful for treatment of both insulin-dependent or type I diabetes (formerly termed juvenile-onset or ketosis-prone diabetes) and non-insulin-dependent or type II diabetes (formerly termed adult-onset, maturity-onset or nonketotic diabetes).

When administered to a mammal for veterinary use or to a human for clinical use, the extracts can be used alone, or may be combined with any physiologically acceptable carrier such as water, an aqueous solution, normal saline, or other physiologically acceptable excipient. In general, the dosage would range from about 10–1000 mg/kg/day, preferably about 10–250 mg/kg/day.

The extracts can be administered by a number of routes, including, but not limited to: orally, injection including, but not limited to intravenously, intraperitonerally, subcutaneously, intramuscularly, etc. The preferred route of administration is oral. Additionally, the extracts can be administered in conjunction with another hypoglycemic including such as insulin; a biguanide such as metformin or buformin; a sulfonylurea such as acetohexamide, chloropropamide, tolazamide, tolbutamide, glyburide, glypizide or glyclazide; a thiazolidinedione such as troglitazone; an α-glycosidase inhibitor such as acarbose or miglatol; or a β$_3$-adrenoceptor agonist such as CL-316, 243, etc.

According to another embodiment of the invention, compositions comprising a quindoline alkaloid compound having the following structure or a pharmaceutically acceptable salt thereof said compound selected from group consisting of:

(a) where $R_1-R_{11}$=H;

(b) where $R_1-R_4$ and $R_6-R_{11}$=H, and $R_5$=CH$_3$;

(c) where $R_1-R_4$ and $R_6-R_{11}$=H, and $R_5$ is selected from the group of ethyl, isopropyl, benzyl, 4-hydroxybenzyl, 4-dimethylaminobenzyl, 4-chlorobenzyl, phenyl, 2-chlorophenyl, 3-chlorophenyl, 2-bromophenyl, 3-bromophenyl, 2-fluorophenyl, 3-fluorophenyl, 2-iodophenyl, 3-iodophenyl, 4-iodophenyl, 2-hydroxyphenyl, 3-hydroxyphenyl, 2-dimethylaminophenyl, 3-dimethylaminophenyl, 2-methoxyphenyl, 3-methoxyphenyl, 4-methoxyphenyl, 4-hydroxyphenyl, 4-dimethylaminophenyl, 4-chlorophenyl, 2-pyridino, 3-pyridino, 4-pyridino, 2-imidazol, 4-imidazol, 2-hydroxybenzyl, 3-hydroxybenzyl, 2-dimethylaminobenzyl, 3-dimethylaminobenzyl, 2-methoxybenzyl, 3-methoxybenzyl, 4-methoxybenzyl, 2-chlorobenzyl, 3-chlorobenzyl, 2-bromobenzyl, 3-bromobenzyl, 4-bromobenzyl, 2-fluorobenzyl, 3-fluorobenzyl, 4-fluorobenzyl, 2-iodobenzyl, 3-iodobenzyl, 4-iodobenzyl, 2-pyridylmethyl, 3-pyridylmethyl, 4-pyridylmethyl, 2-imidazolylmethyl, 4-imidazolymethyl, 4-bromophenyl, 4-fluorophenyl, cyclopropyl, and isobutyl;

(d) where $R_1$, $R_4$ and $R_6-R_{11}$=H, $R_2$=$R_3$=—CH$_2$—O—CH$_2$—, and $R_5$ is selected from the group consisting of ethyl, isopropyl, benzyl, 4-hydroxybenzyl, 4-dimethylaminobenzyl, 4-chlorobenzyl, phenyl, 2-chlorophenyl, 3-chlorophenyl, 2-bromophenyl, 3-bromophenyl, 2-fluorophenyl, 3-fluorophenyl, 2-iodophenyl, 3-iodophenyl, 4-iodophenyl, 2-hydroxyphenyl, 3-hydroxyphenyl, 2-dimethylaminophenyl, 3-dimethylaminophenyl, 2-methoxyphenyl, 3-methoxyphenyl, 4-methoxyphenyl, 4-hydroxyphenyl, 4-dimethylaminophenyl, 4-chlorophenyl, 2-pyridino, 3-pyridino, 4-pyridino, 2-imidazol, 4-imidazol, 2-hydroxybenzyl, 3-hydroxybenzyl, 2-dimethylaminobenzyl, 3-dimethylaminobenzyl, 2-methoxybenzyl, 3-methoxybenzyl, 4-methoxybenzyl, 2-chlorobenzyl, 3-chlorobenzyl, 2-bromobenzyl, 3-bromobenzyl, 4-bromobenzyl, 2-fluorobenzyl, 3-fluorobenzyl, 4-fluorobenzyl, 2-iodobenzyl, 3-iodobenzyl, 4-iodobenzyl, 2-pyridylmethyl, 3-pyridylmethyl, 4-pyridylmethyl, 2-imidazolylmethyl, 4-imidazolymethyl, 4-bromophenyl, 4-fluorophenyl, cyclopropyl, and isobutyl;

(e) where $R_1-R_4$ and $R_6-R_7$ and $R_{10}-R_{11}$=H, $R_8$=$R_9$=—CH$_2$O—CH$_2$—, and $R_5$ is selected from the group consisting of ethyl, isopropyl, benzyl, 4-hydroxybenzyl, 4-dimethylaminobenzyl, 4-chlorobenzyl, phenyl, 2-chlorophenyl, 3-chlorophenyl, 2-bromophenyl, 3-bromophenyl, 2-fluorophenyl, 3-fluorophenyl, 2-iodophenyl, 3-iodophenyl, 4-iodophenyl, 2-hydroxyphenyl, 3-hydroxyphenyl, 2-dimethylaminophenyl, 3-dimethylaminophenyl, 2-methoxyphenyl, 3-methoxyphenyl, 4-methoxyphenyl, 4-hydroxyphenyl, 4-dimethylaminophenyl, 4-chlorophenyl, 2-pyridino, 3-pyridino, 4-pyridino, 2-imidazol, 4-imidazol, 2-hydroxybenzyl, 3-hydroxybenzyl, 2-dimethylaminobenzyl, 3-dimethylaminobenzyl, 2-methoxybenzyl, 3-methoxybenzyl, 4-methoxybenzyl, 2-chlorobenzyl, 3-chlorobenzyl, 2-bromobenzyl, 3-bromobenzyl, 4-bromobenzyl, 2-fluorobenzyl, 3-fluorobenzyl, 4-fluorobenzyl, 2-iodobenzyl, 3-iodobenzyl, 4-iodobenzyl, 2-pyridylmethyl, 3-pyridylmethyl, 4-pyridylmethyl, 2-imidazolylmethyl, 4-imidazolymethyl, 4-bromophenyl, 4-fluorophenyl, cyclopropyl, and isobutyl;

(f) where $R_1-R_3$ and $R_6-R_{11}$=H, and $R_4-R_5$=—CH$_2$CH$_2$—;

(g) where $R_1-R_3$ and $R_6-R_{11}$=H, and $R_4-R_5$=—CH$_2$CH$_2$CH$_2$—;

(h) where $R_1-R_4$ and $R_6-R_{11}$=H, $R_5$=CH$_3$, and 10a, 11=dihydro;

(i) where $R_1-R_4$ and $R_6-R_{11}$=H, $R_5$+CH$_3$, and 5a, 5b=dihydro;

(j) where $R_1-R_4$ and $R_6-R_{11}$=H, $R_5$=CH$_3$, and 5a, 5b, 10a, 11=tetrahydro.

(k) where $R_1-R_{11}$=H, and 9a,10=dihydro; and (l) where $R_1-R_{11}$=H, and 10-methyl are advantageously useful in veterinary and human medicine as hypoglycemic agents.

A preferred mode of this embodiment of the invention encompasses methods of administering the cryptolepine or quindoline as hypoglycemic agents.

The quindoline alkaloids, including quindoline or cryptolepine, can be administered in an effective amount either as alkaloids freed from their corresponding salts or pharmaceutically acceptable salts such as hydrochloride, hydrobromide, phosphate, sulfate, acetate, succinate, ascorbate, tartrate, gluconate, benzoate, malate, and fumarate.

The pharmaceutically acceptable salts of cryptolepine and quindoline which are useful for the present invention having the following structure:

R=H, quindoline
R=CH$_3$, cryptolepine
X=conjugate base of acid.

When administered to a mammal for veterinary use or to a human for clinical use, a quindoline alkaloid compound of formula I, including but not limited to quindoline and cryptolepine, or pharmaceutically acceptable salts thereof may be used alone, or may be combined with any physiologically acceptable carrier such as water, an aqueous solution, normal saline, or other physiologically acceptable excipient. In general, the dosage would range from about 1 to about 100 mg/kg body weight of the human or animal to be treated.

The quindoline alkaloid compounds of formula I, including quindoline and cryptolepine, or pharmaceutically acceptable salts thereof can be administered by a number of routes, including, but not limited to: orally, injection including, but not limited to intravenously, intraperitoneally, subcutaneously, intramuscularly, etc. The preferred route of administration is oral. Additionally, the quindoline alkaloid compounds of formula I, including quindoline and cryptolepine, or a phamaceutically acceptable salt thereof, can be administered in conjunction with another hypoglycemic including such as insulin; a biguanide such as metformin or buformin; a sulfonylurea such as acetohexamide, chloropropamide, tolazamide, tolbutamide, glyburide, glypizide or glyclazide; a thiazolidinedione such as troglitazone; and α-glycosidase inhibitor such as acarbose or miglatol; or $\beta_3$-adrenoceptor agonist such as CL-316, 243, etc.

Finally, the quindoline alkaloid compounds of formula I, including quindoline and cryptolepine, or pharmaceutically acceptable salts thereof and compositions containing said quindoline alkaloid compounds of formula I, including quindoline and cryptolepine, or pharmaceutically acceptable salts thereof can be used for research purposes, for example, to investigate the mechanism and activity of hypoglycemic agents.

The following series of Examples are presented by way of illustration and not by way of limitation on the scope of the invention.

6. PREPARATION OF BIOLOGICALLY ACTIVE EXTRACTS

Dried root of *Cryptolepis sanguinolenta* was obtained and an extract prepared according to one embodiment of the present invention as illustrated in FIG. 1. 1 Kg of the root material was finely ground in a Wiley mill and macerated overnight with 10L of dichloromethane (DCM). After filtration, the dichloromethane extract was evaporated to dryness to yield 22.7 g of neutral extractables (2.26 wt. %) (herein designated as fraction DF-229-13-1). The remaining root powder as dried and subsequently wetted with 10% aqueous sodium carbonate solution until the material gained dough consistence. The wetted root material was then lyophilized for three days until powder dry. This material was macerated under gentle stirring for 24 hrs. with 90% aqueous ethanol, filtered, and the filtrate reduced to dryness under vacuum (herein designated as fraction DF-229-13-4). (This extract contained the alkaloids as free bases and showed pronounced antihyperglycemic effect at 250 mg/kg in the C57BL/ks db mouse model). 5 g of fraction DF-229-13-4 were loaded on a chromatography column filled with DOWEX 50X8-400 strongly acidic ion exchange resin and washed subsequently with 10% aqueous ethanol, 95% ethanol and 10% ammonia in methanol to give after evaporation of solvents 1.95 g (39 wt. %) of aqueous ethanol eulate (herein designated as fraction DF-229-19-1), 0.3 g(6 wt. %) of ethanol eluate (herein designated as fraction DF-229-19-2), and 2.3 g (46 wt. %) of methanolic ammonia eluate (herein designated as fraction DF-229-19-3). Proton and carbon nuclear magnetic resonance spectroscopy (NMR) of the fraction DF-229-19-3 showed that the fraction contained cryptolepine and quindoline in a ratio of approximately 1:1. Fraction DF-229-19-3 was then loaded onto a highly crosslinked polymethacrylate HPLC column and separated following gradient elution by a water/acetonitrile/isopropanol gradient. More particularly, the HPLC column used over a YMC-Pack 250 mm×4.6 mm Polymer C18 6 μm pore size. The flow rate was 1 ml/min. The solvent system is shown below in Table 1.

TABLE 1

| HPLC SOLVENT SYSTEM | | | |
|---|---|---|---|
| Time (min) | % H$_2$O | % Acetonitrile | % Isopropanol |
| 00.0 | 80 | 20 | 0 |
| 13.0 | 100 | 0 | 0* |
| 15.00 | 100 | 0 | 0 |
| 15.10 | 0 | 30 | 70* |
| 25.20 | 0 | 30 | 70 |

*Linear Gradient

Detection used was: Rainin UV-1 detector at 254 nm. Retention time of Peak I was 12.3 min.; Peak II, 14.4 min. (See FIG. 1). Although not desiring to be limited to a particular structure for the hypoglycemic agent of Peaks I and II, the NMR spectra of these peaks are consistent, respectively, with cryptolepine and quindoline. Two peaks, corresponding, respectively, to cryptolepine and quindoline in a 1:1 ratio, respectively, were collected, concentrated and evaluated for biological activity.

While $^1$H NMR analysis of fraction DF-229-19-3 (infra) suggested a mixture comprised primarily of cryptolepine, the present inventors do not wish to be limited to the use of compounds having the chemical structure of quindoline or cryptolepine. As demonstrated in Section 7 (infra), DF-229-19-3 has hypoglycemic activity associated with the compounds corresponding to peaks I and II.

According to another embodiment of the invention, an extract was prepared as follows. 100 g of dried root of *Cryptolepis sanguinolenta*, in ground or powdered form was percolated overnight, at about 55°C., in 1 L of water. After filtration, the aqueous extract was evaporated to dryness to yield a hypoglycemic extract of the present invention.

7. HYPOGLYCEMIC AND OTHER EFFECTS OF EXTRACTS

The following experiments demonstrate that the extracts of the present invention and quindoline alkaloids, for example, cryptolepine and quindoline, and salts thereof produce a significant and consistent hypoglycemic effect on obese diabetic, i.e., an art recognized model of diabetes mellitus. The experiments also demonstrate reduction of plasma triglyceride in diabetic mice.

7.1 MATERIALS AND METHODS

Animals

Genetically transformed diabetic m ale mice (C57BL/ks db) (Jackson Laboratories, Bar Harbor, Me.) of 8–9 weeks of age served as test animals. In some experiments, littermate lean mice (non-diabetic mice) were also included as test animals. Five animals per cage were housed at 22±3° C. at 50±20% relative humidity. The mice were fed a diet of Purina rodent chow, with water ad libitum. The mice were identified via cage labeling and tail marking.

Methods

Prior to dosing, 20 μL of blood were collected from each animal by tail nick. Plasma glucose levels were determined by the glucose oxidase method colorimetrically (Sigma test kit, cat.#315, Sigma Chemical Co., St. Louis, Mo.). These values were used as predose levels. Animals with plasma glucose levels below 300 mg/dL were eliminated from the study, while the remaining ones were randomized into group of 5 with mean glucose levels of not more than 20 mg/dL of difference. Body weight and food consumption were measured daily during the experiment period.

Extracts or purified compounds were either dissolved or suspended in liquid solvent as indicated and administered, orally to test animals using a 20 gauge feeding needle and a 1 mL syringe. The dose volume was 10 mL/kg. Blood samples were collected at specified intervals. Plasma glucose levels were measured immediately after bleeding. In some experiments, plasma triglyceride levels were measured using an enzymatic colorimetric assay (Triglyceride Diagnostic Kit, Sigma, cat #339 (Sigma Chemical Co., St. Louis, Mo.).

7.2 EXPERIMENTS

Figure 2:
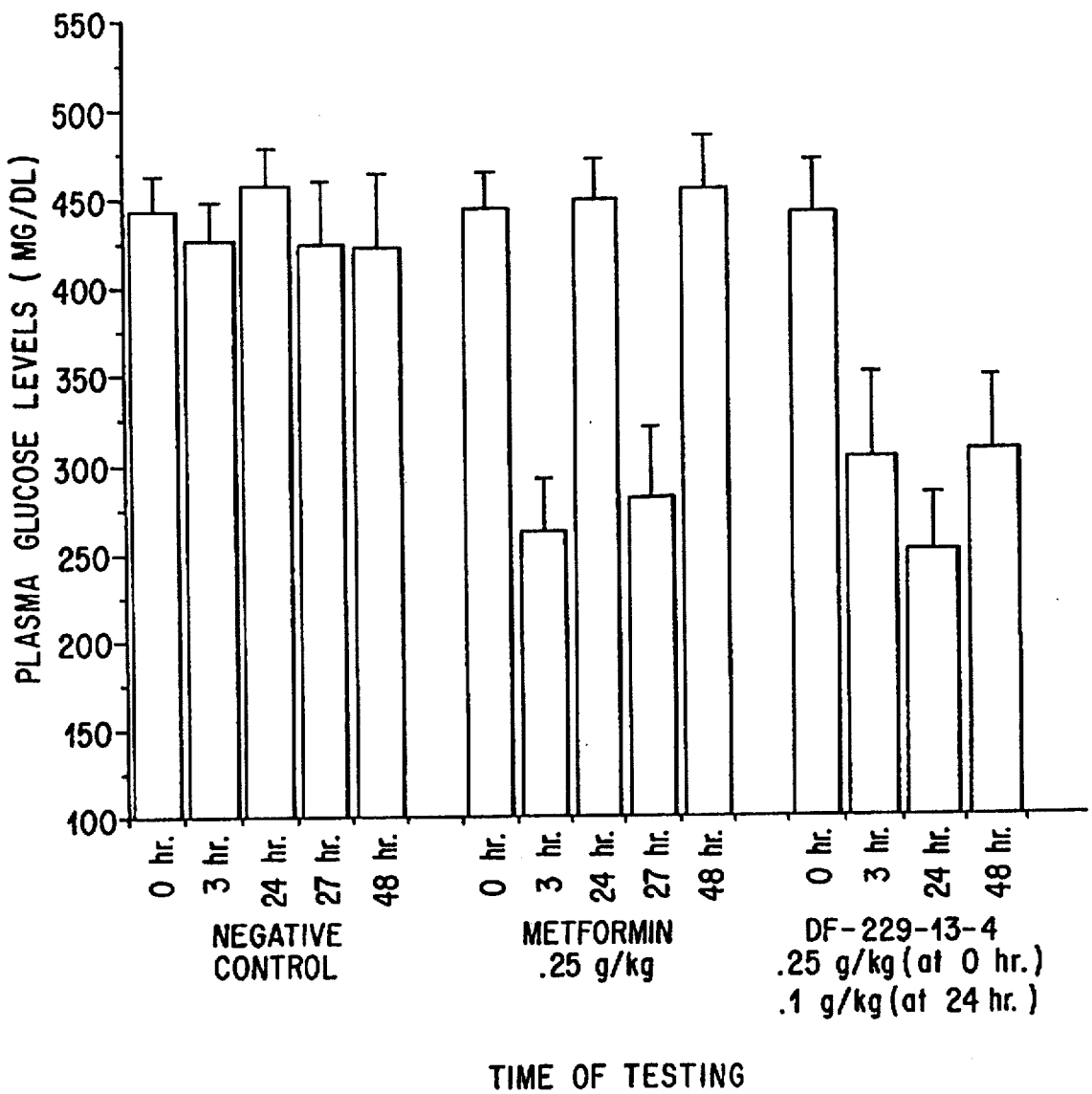
FIG. 2 is a histogram illustrating the anti-hyperglycemic activity of DF-229-13-4, a fraction from the extract as illustrated in FIG. 1.

Animal experiments were conducted using fractions of an extraction of Cryptolepis sp. as illustrated in FIG. 1, generally as described in Section 7.1. In one experiment, DF-229-13-4 and metformin were separately suspended in aliquots of 0.25 wt. % carboxymethyl cellulose +1% TWEEN™ 60 (Vehicle). Three groups of 5 animals (C57BL/ks db mice) were used. DF-229-13-4 was administered at 250 mg/kg at 0 hr and at 100 mg/kg at 24 hrs.; metformin at 250 mg/kg at 0 hr and 24 hrs (positive control); Vehicle at 10 mL/kg at 0 hr and 24 hrs (negative control). The results are shown in FIG. 2.

As illustrated, administration of fraction DF-229-13-4, administered at 250 mg/kg at 0 hrs. and at 100 mg/kg at 24 hrs., reduced the plasma glucose from a basal level of approx. 440 mg/kL to approx. 300 mg/dL after 3 hrs. and approx. 250 mg/dL after 24 hrs.

Figure 3:
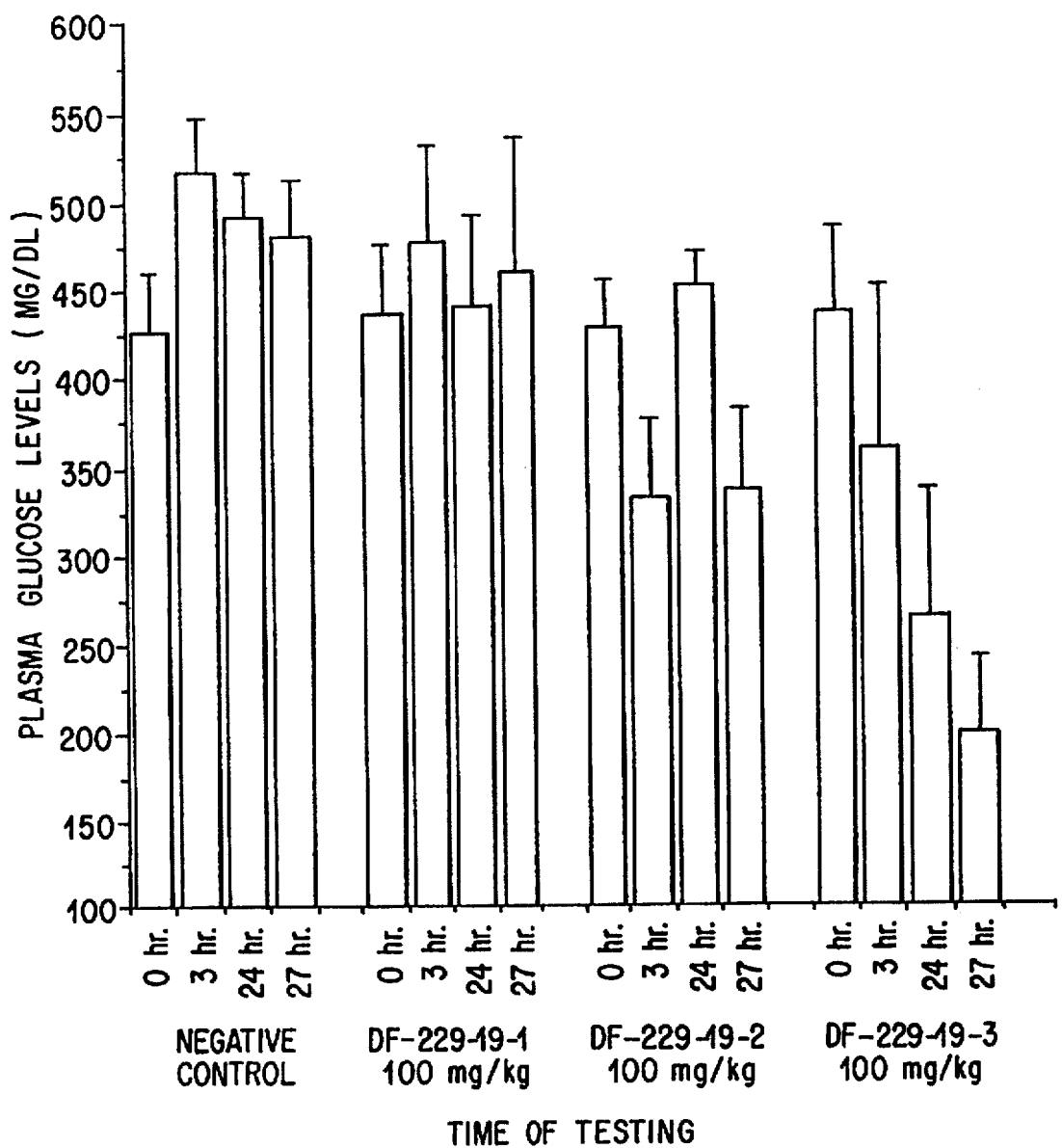
FIG. 3 is a histogram illustrating the anti-hyperglycemic activity of DF-229-19-3, a fraction from the extract as illustrated in FIG. 1.

In another experiment, fractions DF-229-19-1, DF-229-19-2 and DF-229-19-3 (see FIG. 1) were administered as described above at 100 mg/kg. Vehicle (0.25% carboxymethyl cellulose+1% TWEEN™ 60) served as the negative control. Plasma glucose was tested at 0, 3, 24 and 27 hrs. The results are presented in FIG. 3.

Fraction DF-229-19-3, the most active, reduced the plasma glucose from a basal level of approx. 435 mg/dL to approx. 262 mg/dL after 24 hrs. and to approx. 197 mg/dL after 27 hrs. Fraction DF-229-19-2 was also active in lowering glucose levels but its pattern of activity was different from that of fraction DF-229-19-3.

In another experiment hypoglycemic effects of cryptolepine and quindoline, obtained as Peaks I and II illustrated in FIG. 1 (see Section 6 above), were assessed generally as described in Section 7.1. Four groups of experimental animals were included. Group A, negative control received 0.25% carboxymethyl cellulose (CMC); Group B, positive control, 250 mg/kg metformin; Group C, cryptolepine, 100 mg/kg; and Group D, guindoline, 100 mg/kg, via oral administration. Blood glucose was tested at 0, 3 and 24 hrs. post-administration. The results are shown in FIG. 4.

Figure 4:
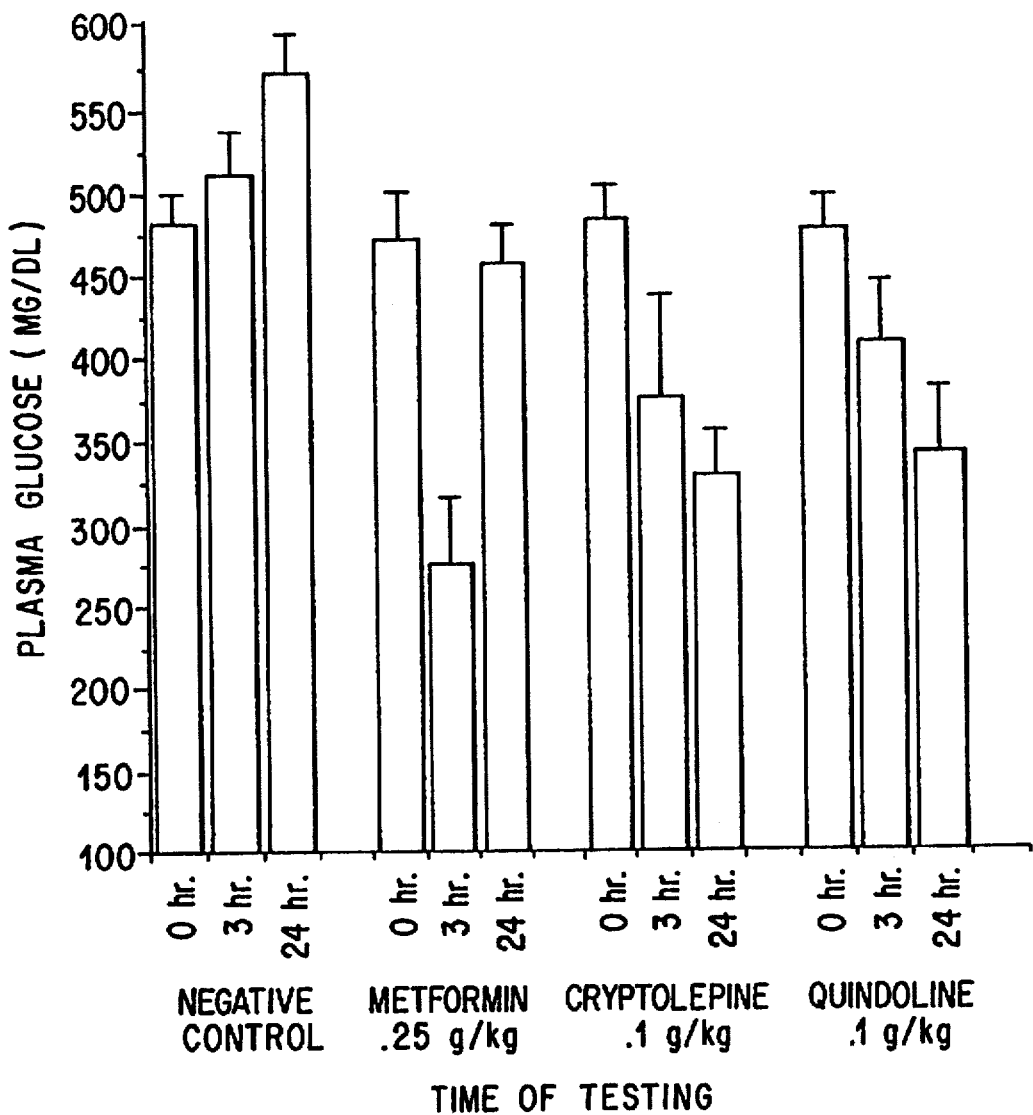
FIG. 4 is a histogram illustrating the anti-hyperglycemic activity of cryptolepine and quindoline in C57BL/ks db mice.

As demonstrated in FIG. 4, both cryptolepins and quindoline, administered at 100 mg/kg, are more effective than metformin, administered at 250 mg/kg, in reducing plasma glucose levels after 24 hrs. Cryptolepine and quindoline reduced the plasma glucose from a basal level of approx. 475 mg/dL to approx. 325 mg/dL, whereas with metformin, the plasma glucose level returned to the basal value after 24 hrs.

In another experiment, the hypoglycemic effect of various doses of cryptolepine was evaluated in genetically transformed obese diabetic male mice (C57BL/ks db) and their littermate lean, non-diabetic mice 8 weeks of age, obtained from Jackson Laboratories, Bar Harbor, Me.

Vehicle (0.25% CMC +1% TWEEN™ 60) was administered orally as a negative control; metformin, at 250 mg/kg as a positive control, and cryptolepine, at various doses, i.e., 10, 30 and 100 mg/kg. All compositions were administered in 0.25% CMC+1% TWEEN™ in deionized water. Each solution was sonicated for 1 minute with a Bransonic ultrasonic tip. The dosage was via oral route. The dosing volume was 10 mL/kg body weight.

All compositions were administered at 0, 24 and 48 hrs. Blood samples were collected at 0, 3, 24, 27, 48 and 51 hours. Plasma glucose and triglyceride levels were measured immediately after bleeding.

Results are presented in FIGS. 5(A–B) for plasma glucose levels and 6(A–B) for triglyceride levels in both diabetic and normal animals.

Figure 5A:
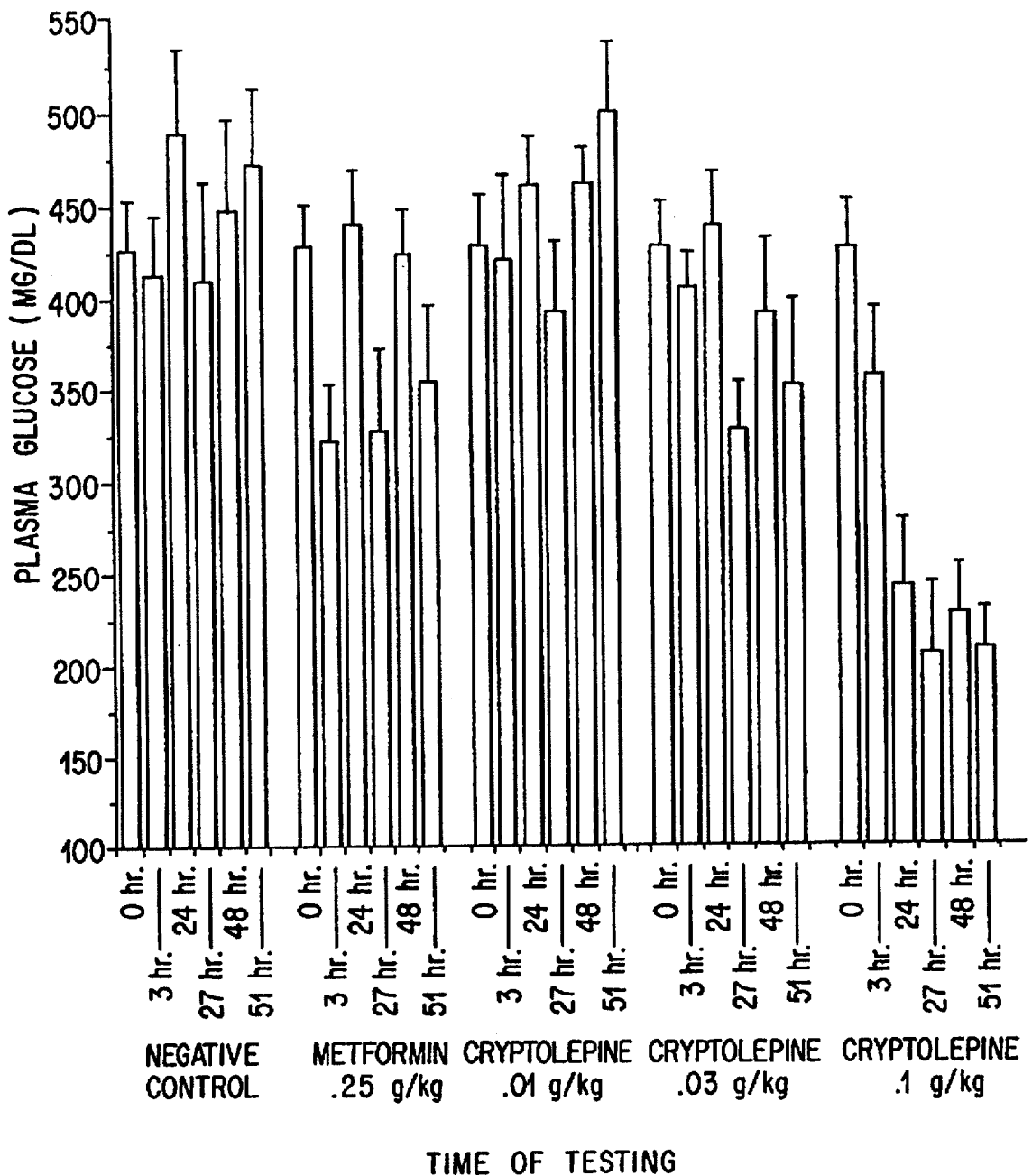
FIG. 5(A–B) is a histogram illustrating the effects of cryptolepine at various doses on plasma glucose levels in: A, diabetic mice and B, lean normal mice.
Figure 5B:
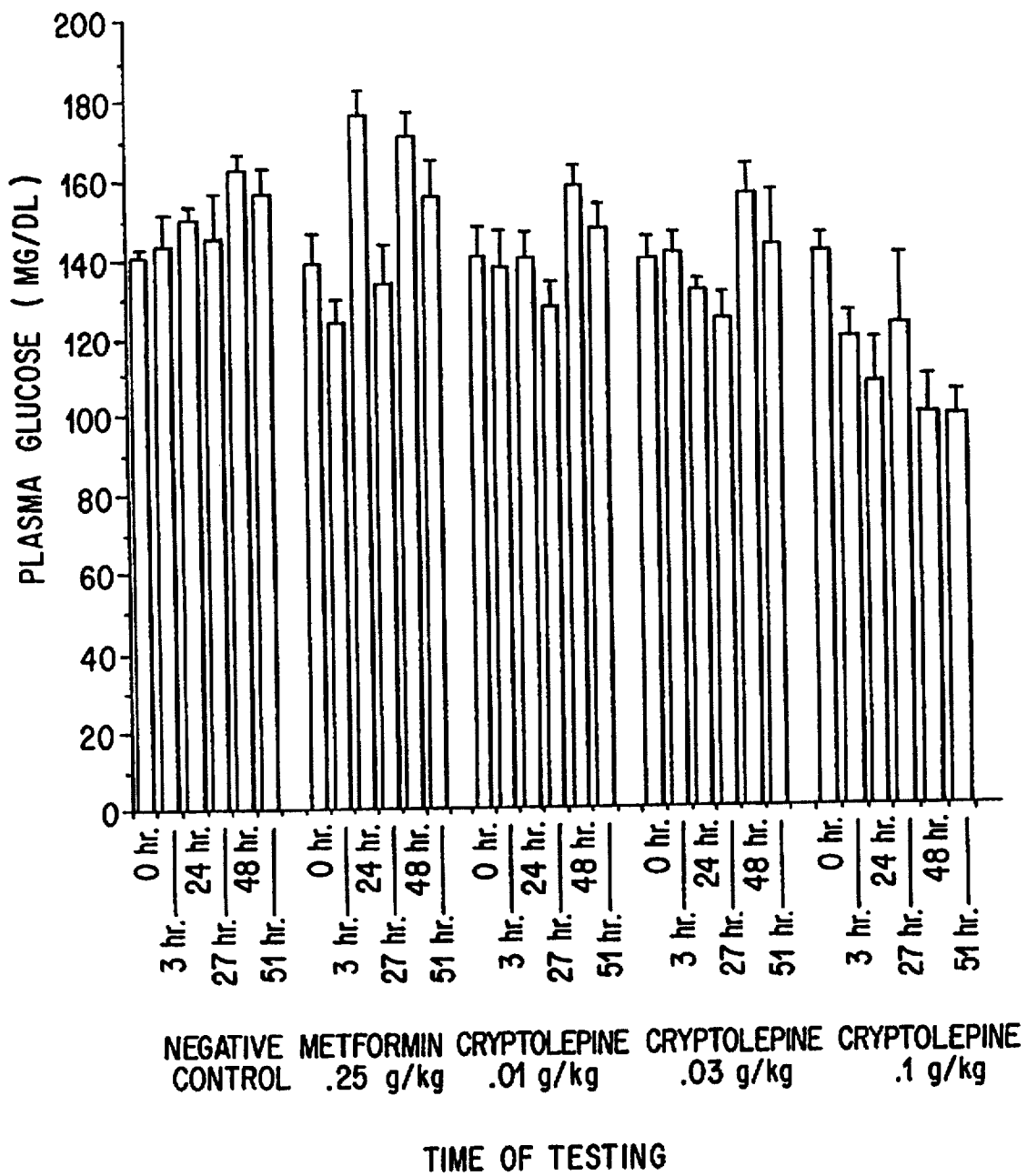

The results in FIG. 5A show that the administration of cryptolepine to diabetic (C57BL/ks db) mice at 30 mg/kg resulted in approximately the same reduction of plasma glucose levels as a 250 mg/kg administration of metformin. Moreover, a 100 mg/kg administration of cryptolepine lowered the blood sugar from a basal value of approx. 425 mg/dL to approx. 250 mg/dL after 24 hrs. and to approx. 225 mg/kg after 27 hrs. Results in FIG. 5B show that administration of 30 mg/kg of cryptolepine to normal lean mice did not effect the blood sugar. Although 100 mg/kg of cryptolepine lowered the blood glucose from a basal value of approx. 140 mg/dL to approx. 110 mg/dL after 24 hrs., further dosing did not affect the glucose level. Thus, the results indicate that cryptolepine significantly lowered glucose levels and gives a dose-dependent anti-diabetic effect.

Figure 6A:
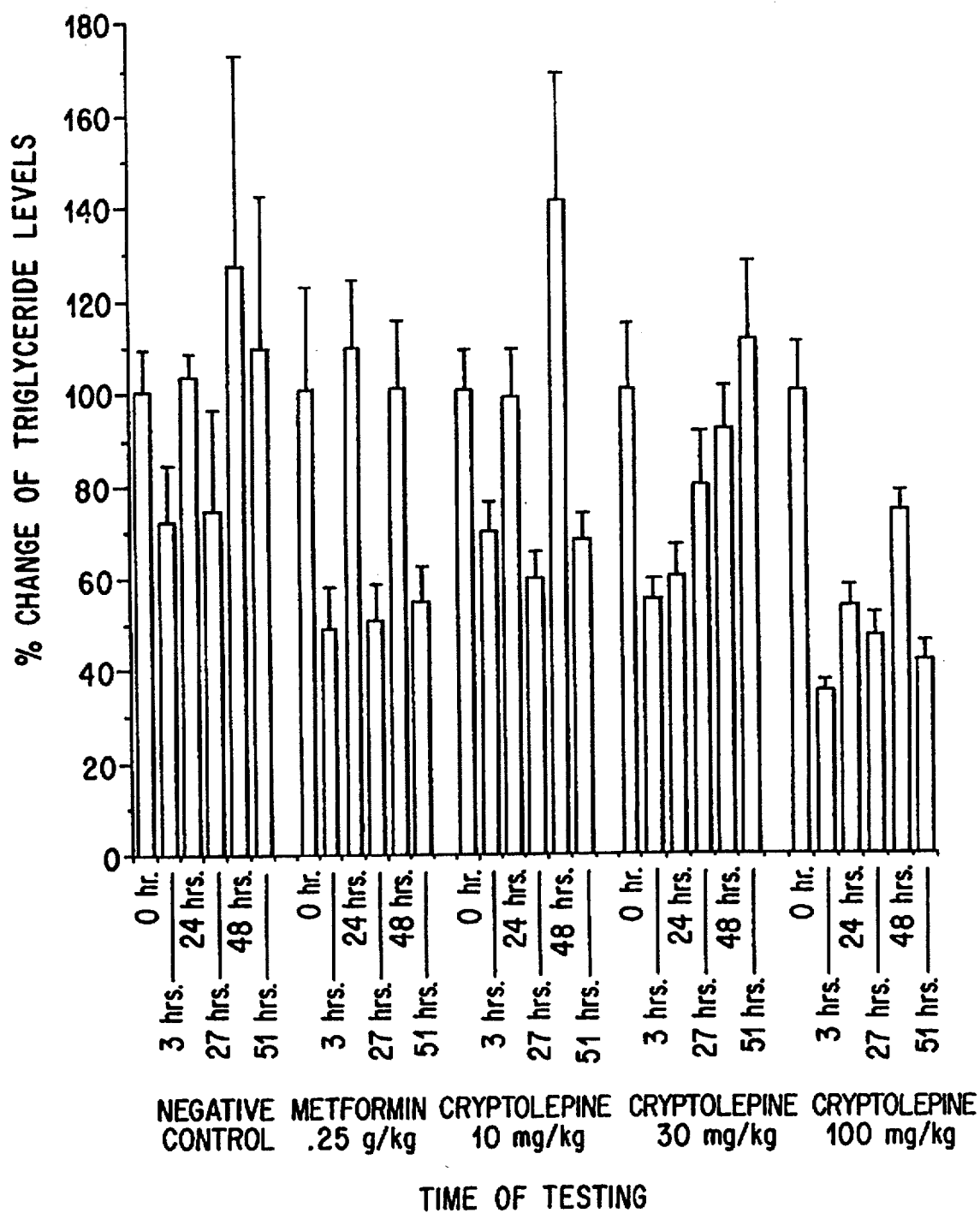
FIG. 6(A–B) is a histogram illustrating the effects of cryptolepine at various doses on triglyceride levels in: A, C57BL/ks db mice, and B, lean normal mice.

The results shown in FIG. 6A indicate that after 3 hrs., cryptolepine administered to diabetic C57BL/ks db mice at a level of 100 mg/kg lowered triglyceride levels to 30% of basal triglyceride levels, as compared to only 50% with a 250 mg/K administration of metformin. In addition, an Analysis of Variance was used to analyze the data presented in FIG. 6A. A comparison between treatment groups and the negative control was made. The results indicate that cryptolepine and metformin both significantly lowered the triglyceride levels.

Figure 6B:
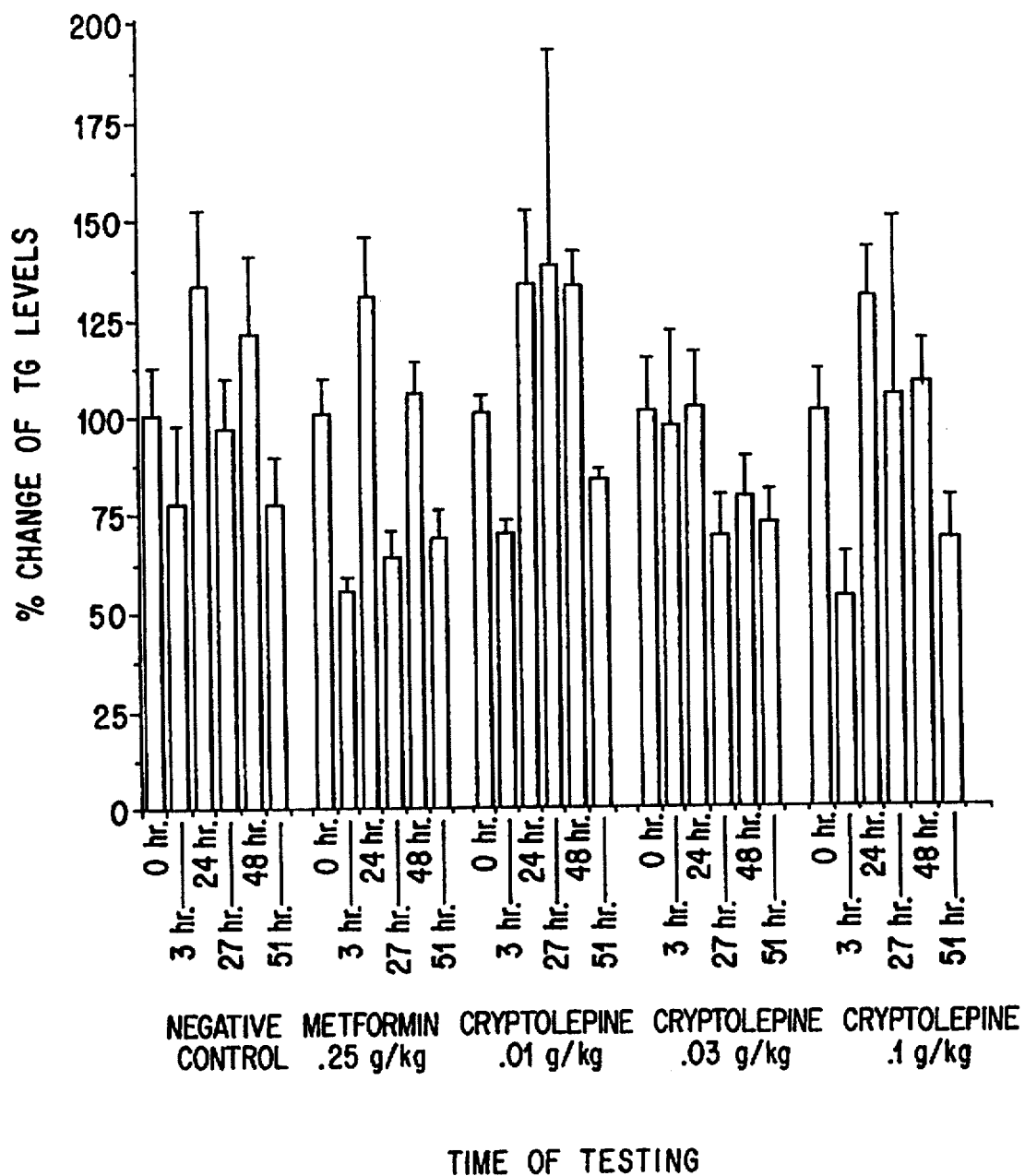

After 3 hrs., cryptolepine administered at 100 mg/Kg to lean non-diabetic mice (see FIG. 6B) resulted in a change of plasma triglyceride levels comparable to those with metformin at 250 mg/Kg. An Analysis of Variance indicated, however, that none of the treatments significantly affected triglyceride levels in the non-diabetic animals.

In yet another series of experiments, hypoglycemic effects of aqueous extracts of the present invention were demonstrated using genetically transformed obese diabetic male mice (C57BL/ks db) of 8 weeks of age, obtained from Jackson Laboratories, Bar Harbor, Me. The experiments were conducted generally as described above in Section 7.1. The aqueous extract was prepared as described in Section 6, above.

Group A, negative control received 0.25%. % CMC; Group B, positive control, metformin at 250 mg/kg; Group C. aqueous extract, at 250 mg/kg; and Group D, aqueous extract, at 1000 mg/kg. All compositions were administered via oral route in 0.25% wt. % CMC in deionized water.

The dosing time was daily from day 1 to day 15. Blood samples were collected at day 0, 3, 8, 12 and 15, 3 hrs. after daily dosing. An additional blood sample was collected on day 8 at 6 hrs. after dosing. Plasma glucose levels were measured immediately after bleeding. For this study, the number of animals used (N)=8.

Figure 7:
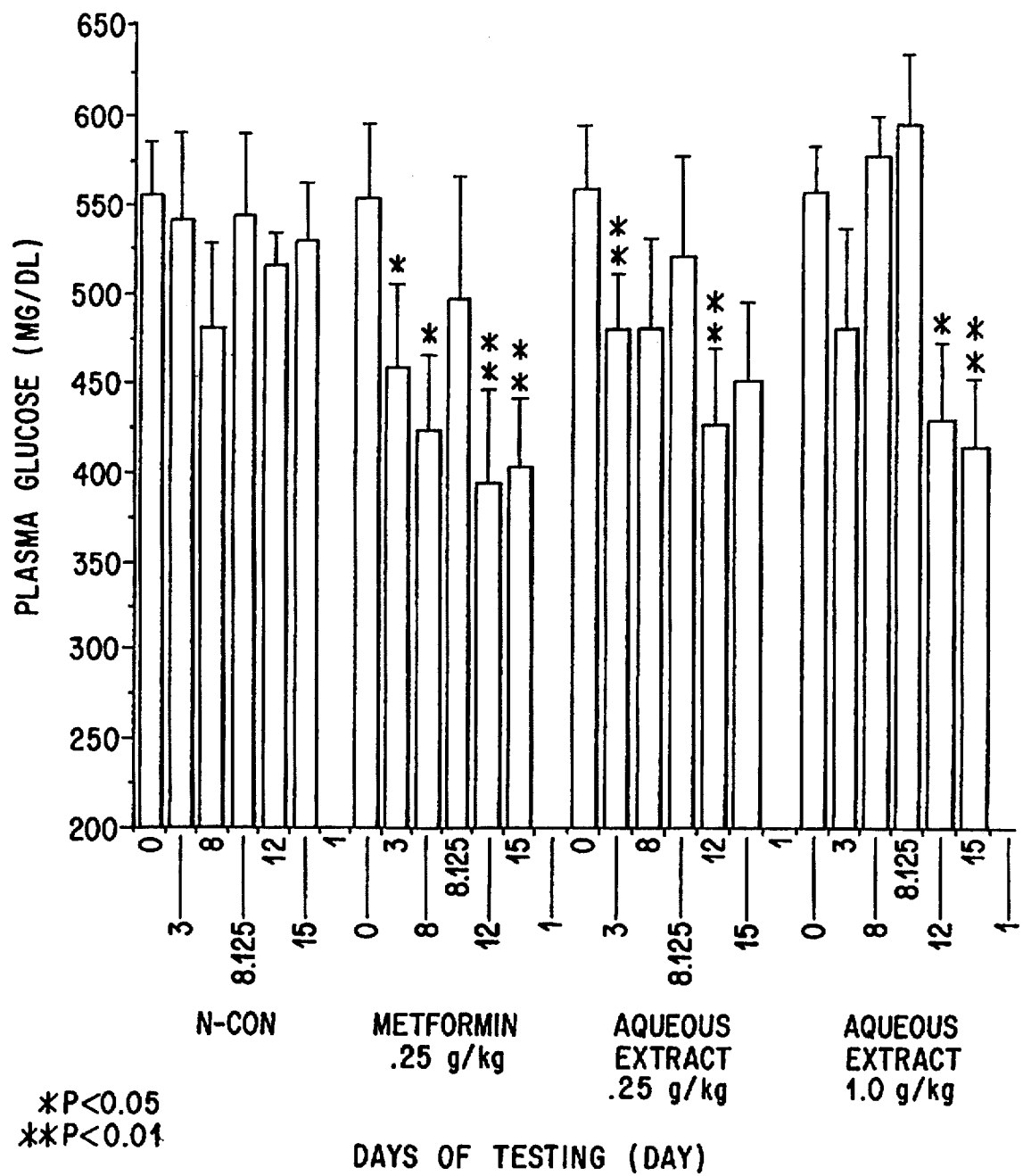
FIG. 7 is a histogram illustrating the anti-hyperglycemic activity of a water extract (roE1) in C57BL/ks db mice.

Results are presented in FIG. 7.

The results illustrated in FIG. 7 show that the administration of the aqueous extract to C57BL/ks db mice at 25 mg/Kg resulted in approximately the same reduction of plasma glucose level as a 250 mg/Kg administration of metformin. Moreover, a 250 mg/Kg administration of the aqueous extract lowered the blood sugar from a basal value of approx. 550 mg/dL to approx. 425 mg/dL after 12 days. These results are comparable with those received obtained using metformin administered at 250 mg/Kg.

The present invention is not to be limited in scope by the specific embodiment disclosed in the examples which are intended as illustrations of a few aspects of the invention and any embodiments which are functionally equivalent are within the scope of this invention. Indeed various modifications of the invention in addition to those shown and described herein will become apparent to those skilled in the art and are intended to fall within the appended claims.

A number of references have been cited and the entire disclosures of which are incorporated herein by reference.

What is claimed is:

1. A compound having the formula:

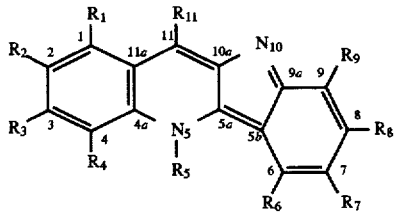

said compound selected from group consisting of:

(a) where $R_1$–$R_3$, $R_6$–$R_9$ and $R_{11}$=H, and $R_4$–$R_5$=—$CH_2CH_2$— and (b) where $R_1$–$R_3$, $R_6$–$R_9$ and $R_{11}$=H, and $R_4$–$R_5$=—$CH_2CH_2CH_2$—.

* * * * *